(12) United States Patent
Wood et al.

(10) Patent No.: US 11,553,981 B2
(45) Date of Patent: Jan. 17, 2023

(54) DIGITAL-BASED MEDICAL DEVICES

(71) Applicant: Welch Allyn, Inc., Skaneateles Falls, NY (US)

(72) Inventors: Robert J. Wood, Marco Island, FL (US); Raymond A. Lia, Auburn, NY (US); Jon R. Salvati, Skaneateles, NY (US); Robert L. Vivenzio, Auburn, NY (US); Ian K. Edwards, Teton Village, WY (US); Ervin Goldfain, Syracuse, NY (US); Colin J. Wolff, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 757 days.

(21) Appl. No.: 16/270,750

(22) Filed: Feb. 8, 2019

(65) Prior Publication Data

US 2019/0167378 A1    Jun. 6, 2019

Related U.S. Application Data

(63) Continuation of application No. 15/589,173, filed on May 8, 2017, now Pat. No. 10,238,462, which is a
(Continued)

(51) Int. Cl.
*A61B 90/00* (2016.01)
*A61B 3/14* (2006.01)
(Continued)

(52) U.S. Cl.
CPC .......... *A61B 90/361* (2016.02); *A61B 1/0011* (2013.01); *A61B 1/00011* (2013.01);
(Continued)

(58) Field of Classification Search
CPC ....... A61B 90/361; A61B 1/227; A61B 1/233; A61B 1/267; A61B 1/303; A61B 1/31;
(Continued)

(56) References Cited

U.S. PATENT DOCUMENTS 3,586,424 A    6/1971  Schenk et al.
3,614,214 A   10/1971  Cornsweet et al.
(Continued)

FOREIGN PATENT DOCUMENTS

DE    19744131 A1    4/1998
EP     1152687 B1    9/2004
(Continued)

OTHER PUBLICATIONS

U.S. Appl. No. 29/207,233, filed Jun. 10, 2004, Fitch et al.
(Continued)

*Primary Examiner* — Jack Dinh
(74) *Attorney, Agent, or Firm* — Barclay Damon LLP

(57) ABSTRACT

A skin measuring microscope includes a housing, an electronic imager disposed along an imaging axis, and an illumination system. The illumination system includes a plurality of LEDs disposed in a ring-like configuration adjacent a distal end of the housing.

17 Claims, 29 Drawing Sheets

Related U.S. Application Data continuation of application No. 14/592,195, filed on Jan. 8, 2015, now Pat. No. 9,642,517, which is a continuation of application No. 13/673,822, filed on Nov. 9, 2012, now Pat. No. 8,944,596.

(60) Provisional application No. 61/557,864, filed on Nov. 9, 2011.

(51) Int. Cl.

| | | |
|---|---|---|
| A61B 1/227 | (2006.01) | |
| A61B 3/12 | (2006.01) | |
| A61B 1/00 | (2006.01) | |
| A61B 5/00 | (2006.01) | |
| A61B 1/06 | (2006.01) | |
| A61B 1/12 | (2006.01) | |
| A61B 3/00 | (2006.01) | |
| A61B 1/31 | (2006.01) | |
| A61B 90/20 | (2016.01) | |
| A61B 90/30 | (2016.01) | |
| A61B 1/233 | (2006.01) | |
| A61B 1/267 | (2006.01) | |
| A61B 1/303 | (2006.01) | |

(52) U.S. Cl.
CPC ........ *A61B 1/0019* (2013.01); *A61B 1/00034* (2013.01); *A61B 1/00039* (2013.01); *A61B 1/00052* (2013.01); *A61B 1/00186* (2013.01); *A61B 1/0684* (2013.01); *A61B 1/128* (2013.01); *A61B 1/227* (2013.01); *A61B 1/233* (2013.01); *A61B 1/267* (2013.01); *A61B 1/303* (2013.01); *A61B 1/31* (2013.01); *A61B 3/0025* (2013.01); *A61B 3/1208* (2013.01); *A61B 3/14* (2013.01); *A61B 5/0077* (2013.01); *A61B 5/441* (2013.01); *A61B 5/6898* (2013.01); *A61B 90/20* (2016.02); *A61B 90/30* (2016.02); *A61B 1/00036* (2013.01); *A61B 2090/061* (2016.02); *A61B 2090/309* (2016.02); *A61B 2090/363* (2016.02); *A61B 2090/3612* (2016.02); *A61B 2090/372* (2016.02); *A61B 2090/373* (2016.02); *A61B 2090/3937* (2016.02); *A61B 2560/0214* (2013.01); *A61B 2560/0431* (2013.01); *A61B 2560/0493* (2013.01); *A61B 2562/146* (2013.01); *A61B 2562/227* (2013.01); *A61B 2576/00* (2013.01); *Y10T 29/49002* (2015.01)

(58) Field of Classification Search
CPC ..... A61B 3/1208; A61B 5/0077; A61B 90/30; A61B 90/20; A61B 5/441; A61B 3/14; A61B 3/0025; A61B 6/6898; A61B 1/00011

See application file for complete search history.

(56) References Cited

U.S. PATENT DOCUMENTS

| | | |
|---|---|---|
| 3,638,641 A | 2/1972 | Abromavage et al. |
| 3,698,099 A | 10/1972 | Matsura |
| 3,698,387 A | 10/1972 | Moore et al. |
| 3,840,004 A | 10/1974 | Heine |
| 3,893,447 A | 7/1975 | Hochheimer et al. |
| 3,914,032 A | 10/1975 | Takano et al. |
| 4,132,456 A | 1/1979 | Matsumura |
| 4,252,420 A | 2/1981 | Kohayakawa |
| 4,265,518 A | 5/1981 | Matsumura |
| 4,366,811 A | 1/1983 | Riester |
| 4,422,736 A | 12/1983 | Nunokawa |
| 4,439,024 A | 3/1984 | Ito |
| 4,564,273 A | 1/1986 | Iba et al. |
| 4,567,881 A | 2/1986 | Heller |
| 4,662,360 A | 5/1987 | O'Hara et al. |
| 4,679,919 A | 7/1987 | Itoh et al. |
| 4,682,866 A | 7/1987 | Volk |
| 4,721,378 A | 1/1988 | Volk |
| 4,785,796 A | 11/1988 | Mattson |
| 4,856,872 A | 8/1989 | Spitznas et al. |
| 4,997,419 A | 3/1991 | Lakatos et al. |
| 5,070,883 A | 12/1991 | Kasahara |
| 5,093,719 A | 3/1992 | Prescott |
| 5,255,025 A | 10/1993 | Volk |
| 5,363,839 A | 11/1994 | Lankford |
| 5,390,663 A | 2/1995 | Schaefer |
| 5,424,789 A | 6/1995 | Volk |
| 5,579,063 A | 11/1996 | Magnante et al. |
| 5,624,453 A | 4/1997 | Ahmed |
| 5,658,235 A | 8/1997 | Priest et al. |
| 5,713,047 A | 1/1998 | Kohayakawa |
| 5,720,756 A | 2/1998 | Green et al. |
| 5,722,762 A | 3/1998 | Soll |
| 5,751,395 A | 5/1998 | Thall |
| 5,795,067 A | 8/1998 | Fraden et al. |
| 5,842,971 A | 12/1998 | Yoon |
| 5,880,813 A | 3/1999 | Thall |
| 5,919,130 A | 7/1999 | Monroe et al. |
| 5,982,555 A | 11/1999 | Melville et al. |
| 6,019,721 A | 2/2000 | Holmes et al. |
| 6,053,875 A | 4/2000 | Rosenbaum et al. |
| 6,099,537 A | 8/2000 | Sugai et al. |
| 6,106,457 A | 8/2000 | Perkins et al. |
| 6,129,661 A | 10/2000 | Iafrati et al. |
| 6,142,934 A | 11/2000 | Lagerway et al. |
| 6,147,705 A | 11/2000 | Krauter et al. |
| 6,190,310 B1 | 2/2001 | Cook |
| 6,213,938 B1 | 4/2001 | Cook |
| 6,254,271 B1 | 7/2001 | Lin |
| 6,331,156 B1 | 12/2001 | Haefele et al. |
| 6,359,677 B2 | 3/2002 | Itoh et al. |
| 6,383,133 B1 | 5/2002 | Jones |
| 6,425,857 B1 | 7/2002 | Rudischhauser et al. |
| 6,450,970 B1 | 9/2002 | Mahler et al. |
| 6,475,138 B1 | 11/2002 | Schechter et al. |
| 6,511,420 B1 | 1/2003 | Farrell et al. |
| 6,537,208 B1 | 3/2003 | Konno |
| 6,554,765 B1* | 4/2003 | Yarush ............... A61B 1/00039 348/73 |
| 6,692,431 B2 | 2/2004 | Kazakevich |
| 7,029,439 B2 | 4/2006 | Roberts et al. |
| 7,046,379 B2 | 5/2006 | Miller et al. |
| 7,177,088 B2 | 2/2007 | Hirata |
| 7,224,822 B2 | 5/2007 | Heacock |
| 7,290,862 B2 | 11/2007 | Collins et al. |
| 7,399,275 B2 | 7/2008 | Goldfain et al. |
| 7,448,753 B1 | 11/2008 | Chinnock |
| 7,597,443 B2 | 10/2009 | Fujii et al. |
| 7,677,730 B2 | 3/2010 | Shimizu |
| 7,762,950 B2 | 7/2010 | Hirata |
| 7,803,110 B2 | 9/2010 | Goldfain et al. |
| 7,854,510 B2 | 12/2010 | Verdooner et al. |
| 7,901,353 B2 | 3/2011 | Vayser |
| 8,043,211 B2 | 10/2011 | Hirata |
| 8,100,826 B2 | 1/2012 | Mackinnon et al. |
| 8,109,981 B2 | 2/2012 | Gertner et al. |
| 8,152,718 B2 | 4/2012 | Cheng |
| 8,159,153 B2 | 4/2012 | Hum |
| D659,840 S | 5/2012 | Cheng et al. |
| 8,210,680 B2 | 7/2012 | Tanguay, Jr. et al. |
| 8,231,522 B2 | 7/2012 | Endo et al. |
| 8,890,489 B2 | 11/2014 | Wood |
| 9,001,326 B2 | 4/2015 | Goldfain |
| 9,153,994 B2 | 10/2015 | Wood et al. |
| 2001/0014112 A1 | 8/2001 | Yamaka |
| 2002/0085616 A1 | 7/2002 | Yu |
| 2002/0143239 A1 | 10/2002 | Henzler |
| 2002/0188177 A1 | 12/2002 | Miyanaga |
| 2002/0193665 A1 | 12/2002 | Jones |
| 2003/0063386 A1* | 4/2003 | Slawson ............... A61B 3/125 359/600 |

(56) References Cited

U.S. PATENT DOCUMENTS

| | | | |
|---|---|---|---|
| 2003/0139672 A1* | 7/2003 | Cane | A61B 5/443 600/473 |
| 2003/0187331 A1 | 10/2003 | Faludi et al. | |
| 2004/0174498 A1 | 9/2004 | Zorn et al. | |
| 2005/0027168 A1 | 2/2005 | Strom et al. | |
| 2005/0027169 A1 | 2/2005 | Goldfain et al. | |
| 2005/0043588 A1 | 2/2005 | Tsai | |
| 2005/0043591 A1 | 2/2005 | Witte | |
| 2006/0020176 A1 | 1/2006 | Berall | |
| 2006/0159155 A1 | 7/2006 | Lantz et al. | |
| 2006/0167340 A1* | 7/2006 | Pease | G02B 23/2476 600/127 |
| 2006/0183977 A1 | 8/2006 | Ishigami et al. | |
| 2007/0140424 A1* | 6/2007 | Serceki | A61B 6/548 378/62 |
| 2007/0255108 A1 | 11/2007 | Schmitz | |
| 2008/0051637 A1 | 2/2008 | Andreassen et al. | |
| 2008/0079897 A1 | 4/2008 | Goldfain et al. | |
| 2011/0006108 A1* | 1/2011 | Yoshida | G08C 19/36 235/375 |
| 2011/0060184 A1 | 3/2011 | Rothberg et al. | |
| 2011/0234977 A1 | 9/2011 | Verdooner | |
| 2012/0229617 A1 | 9/2012 | Yates et al. | |
| 2013/0083183 A1* | 4/2013 | Cheng | A61B 1/227 348/77 |

FOREIGN PATENT DOCUMENTS

| | | |
|---|---|---|
| EP | 2473092 | 3/2011 |
| SU | 501374 | 10/1976 |
| TW | 201216916 | 5/2012 |
| TW | 201229557 | 7/2012 |
| WO | 99/42760 | 8/1999 |
| WO | 2002/056756 A2 | 7/2002 |
| WO | 2005/053519 A1 | 6/2005 |
| WO | 2007/026158 A1 | 3/2007 |
| WO | 2011/042722 A1 | 4/2011 |
| WO | 2011/047214 A2 | 4/2011 |
| WO | 2011/050496 A1 | 5/2011 |

OTHER PUBLICATIONS

Australian Government, IP Australia, Examiner's First Report on Patent Application No. 2001263366 by Welch Allyn, Inc. dated Dec. 9, 2004, (2 pgs.).

Australian Government, IP Australia, Examiner's Second Report on Patent Application No. 2001263366 by Welch Ally, Inc. dated Dec. 19, 2005, (2 pgs.).

Japanese Patent Office, Examiner's Mailing No. 036153, Notice of Grounds for Rejection dated Jan. 31, 2006 for Japanese Patent Application No. 2000-583418, (3 pgs.).

International Search Report and Written Opinion of the International Searching Authority for International Application No. PCT/US2007/065367, dated Jun. 3, 2008 (11 pgs.).

International Search Report, dated Mar. 10, 2009, PCT/US2008/073956 (4 pgs.).

European Search Report for EP Application No. 08796437.3, dated Oct. 27, 2010, (7 pgs.).

Medimaging Integrated Solution Inc., http://www.miis.com.tw/?option=product&language=zh-tw&mod=5, accessed Apr. 18, 2013, (11 pgs.).

Digital Hand-held Diagnositic Set; Medimaging Integrated Solution, Inc., (3 pgs.).

Rudolf Riester GmbH—medical diagnostic instruments; Source: http://www.riester.de/Home.1+B6Jkw9MSZMPTA_0.html, Date Accessed: Sep. 14, 2012.

Parnes, et al. (1996), Advances in the Development of the Interferometric Otoscope. The Laryngoscope, 106: 263-267, (5 pgs.).

Nishikawa, et al. (2001), A Novel Colonoscope with High Color-Rendering White Light-Emitting Diodes, 73: 598-602. (5 pgs.).

International Search Report and Written Opinion of the International Searching Authority for International Application No. PCT/US2012/084510, dated Apr. 29, 2013 (17 pgs.).

Rajewski, (2012), An Optical Engineering Feat from the Kitchen, Cummings School of Veterinary Medicine at Tufts University (2 pgs.).

All-N1 Video Otoscopy (MD Scope), Source: http://www.jedmed.com/produces/all-n1-video-otoscopy. Date Accessed: Oct. 25, 2011, (2 pgs.).

Dreher, Andreas W., Field Portable digital ophthalmoscope/fundus camera, Laser Diagnostic Technologies, Inc., Jun. 1997 (26 pgs.).

Smithwick et al, Non-Paraxial Design for a Transportable Digital Retinal Imager, http:www.opticasinfobase.org/abstract.cfm?uri=FiO-2004-FWM5.

Optomap Panoramic200, http://www.joneseyecenters.com/index.cfm/technology/optomap, Date Accessed: Feb. 23, 2013 (3 pgs.).

Australian Patent Examination Report for AU201236072; dated May 24, 2016; 2 pages.

European Examination Report for EP 12 791 644.3; dated Apr. 25, 2018; 3 pages.

\* cited by examiner

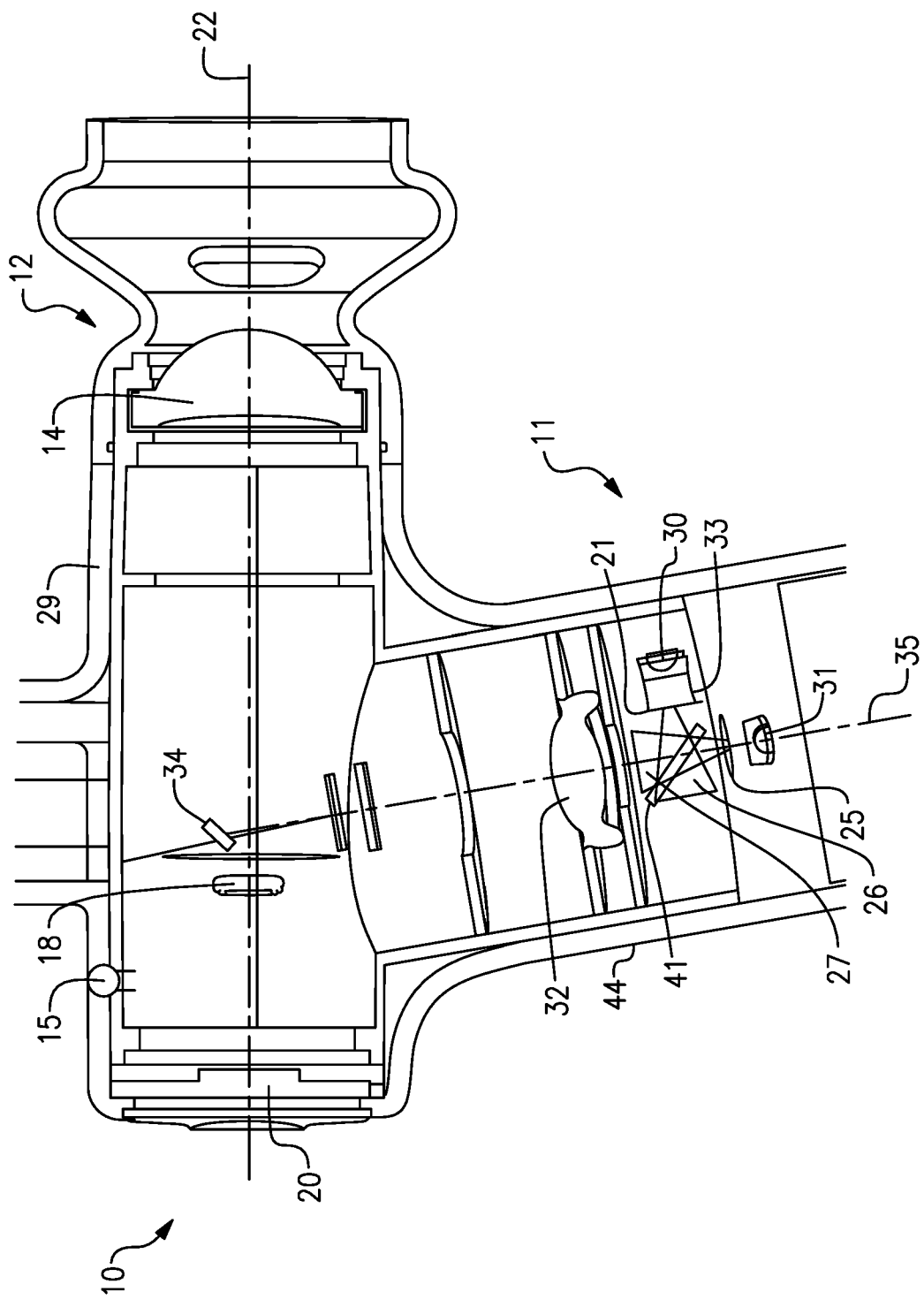

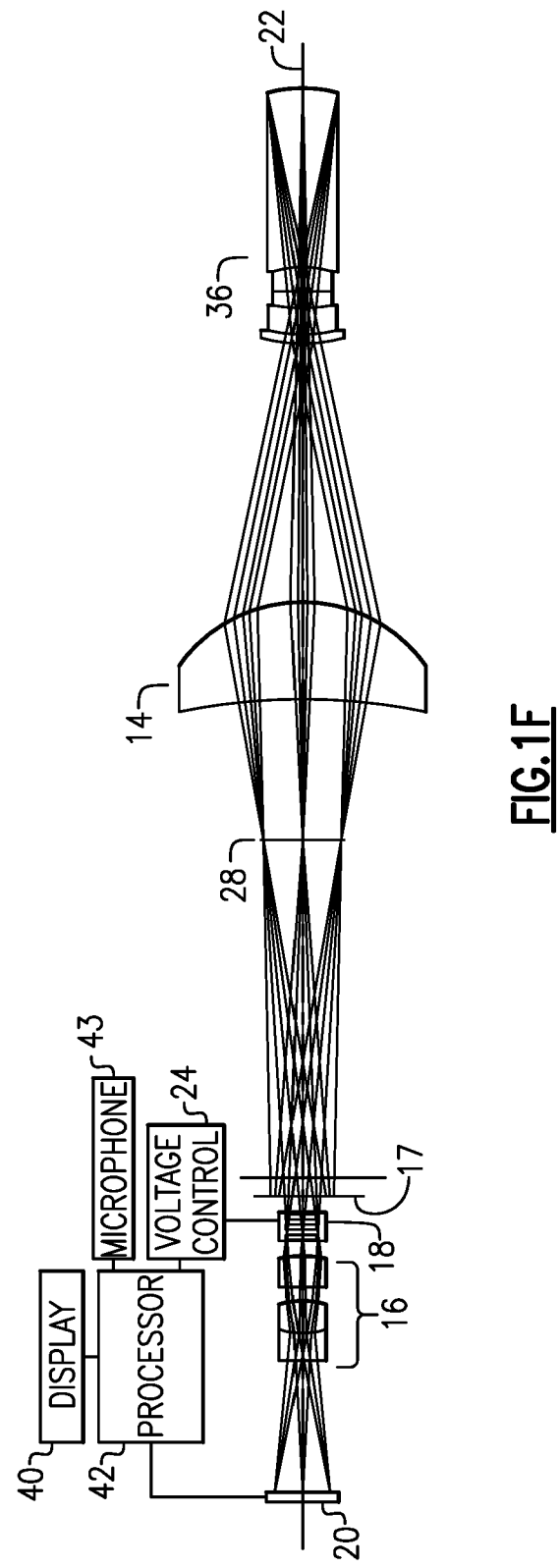

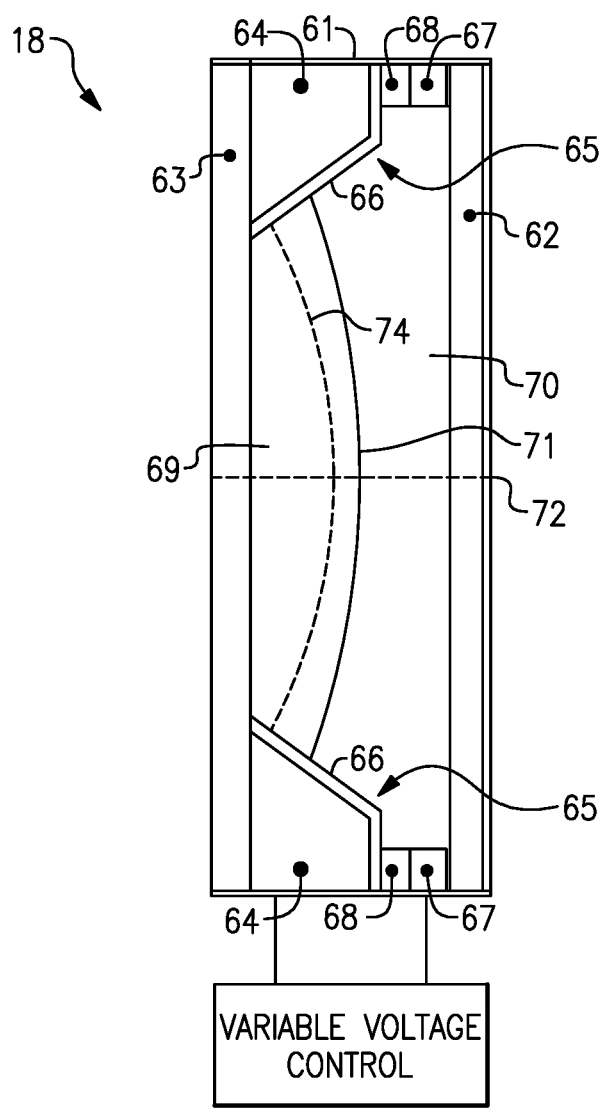
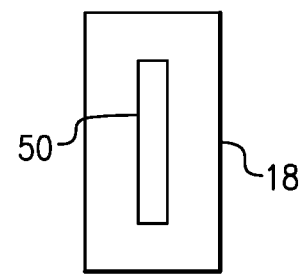
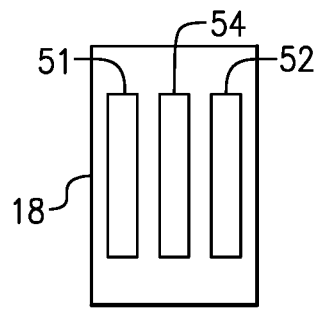
FIG.2A
FIG.2B
FIG.2C

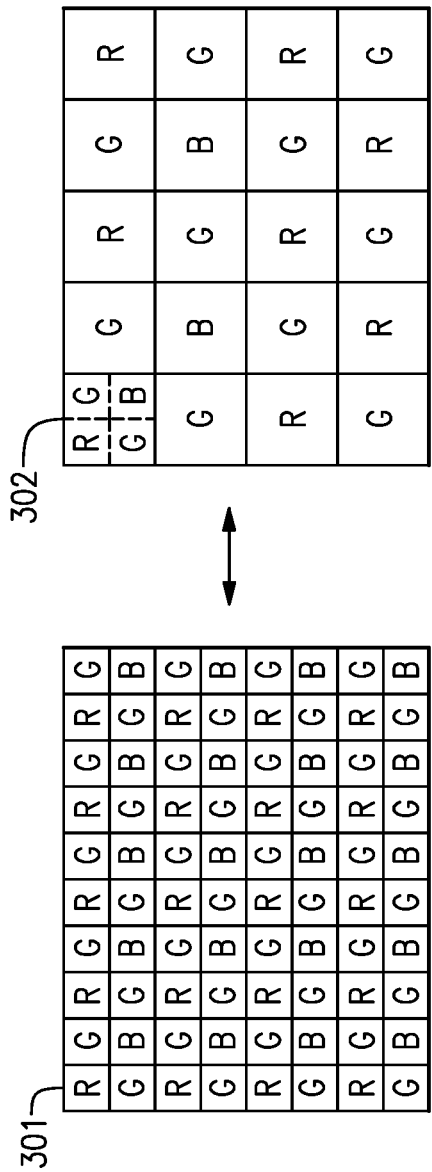
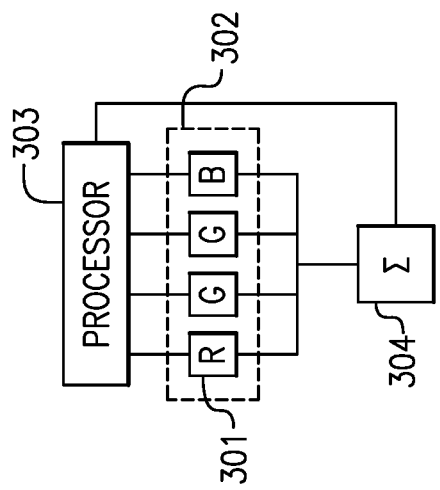
FIG. 3B
FIG. 3A
FIG. 3C

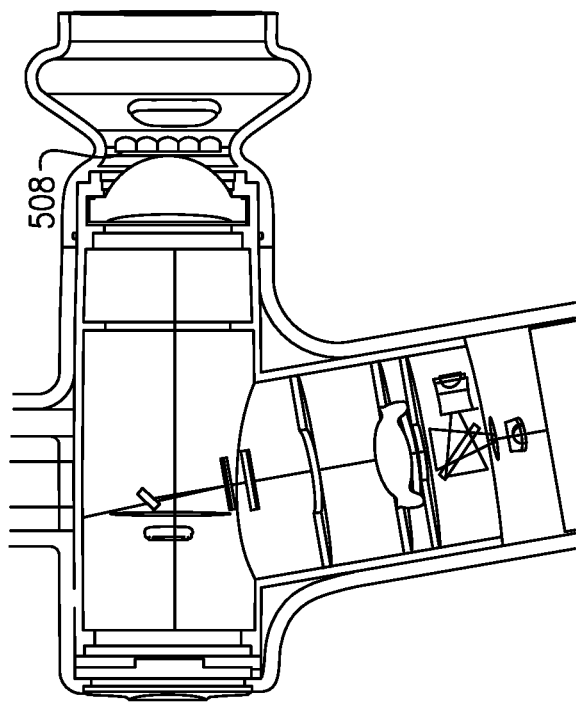
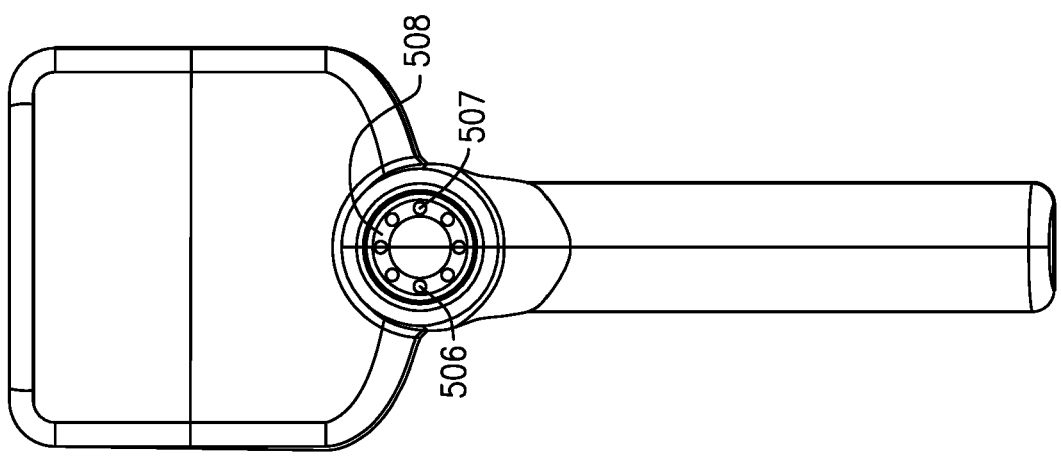
FIG.5C
FIG.5B

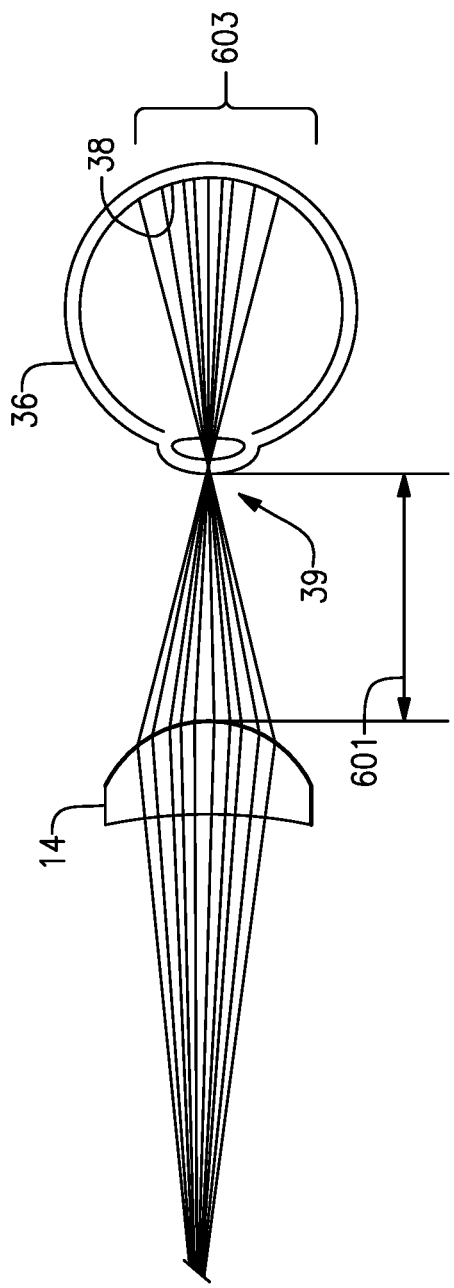
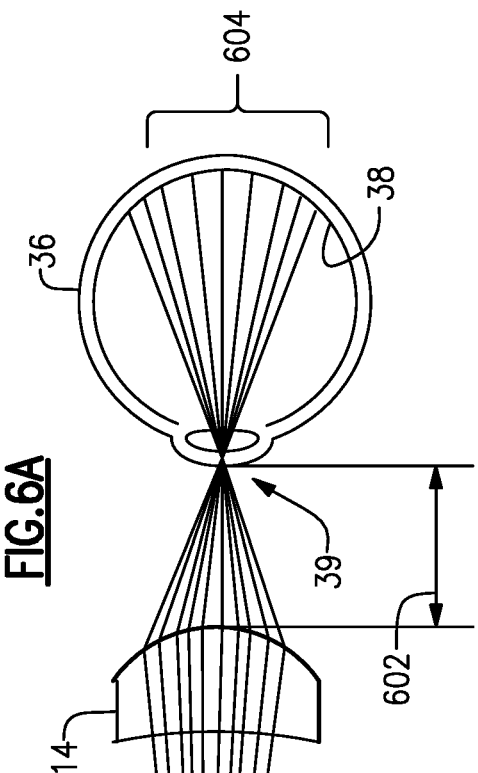

DIGITAL-BASED MEDICAL DEVICES

CROSS REFERENCE TO RELATED APPLICATIONS

This application is a continuation of and claims priority under 35 U.S.C. § 120 to U.S. patent application Ser. No. 15/589,173, filed on May 8, 2017 and entitled: DIGITAL-BASED MEDICAL DEVICES, which is a continuation of U.S. patent application Ser. No. 14/592,195 (now U.S. Pat. No. 9,642,517 B2), filed on Jan. 8, 2015 and entitled, "DIGITAL-BASED MEDICAL DEVICES", which is a continuation of and claims priority to U.S. patent application Ser. No. 13/673,822 (now U.S. Pat. No. 8,944,596 B2) filed on Nov. 9, 2012 and entitled, "DIGITAL-BASED MEDICAL DEVICES", which claims priority to U.S. Provisional Application No. 61/557,864, filed on Nov. 9, 2011 and entitled, "DIGITAL IMAGING DEVICES AND METHODS OF USE", the entire contents of which are incorporated herein by reference.

TECHNICAL FIELD

The application generally relates to the field of diagnostic medicine and more specifically to digitally based medical devices.

BACKGROUND

Numerous types of medical devices are presently known for the purpose of conducting aspects of patient examinations. These devices can include, by way of example, an otoscope used for examining the ear, an ophthalmoscope for examining the eye, a laryngoscope for examining the throat, a skin measuring microscope for examining skin related defects and conditions, and a colposcope for examining the cervix. Hand-held versions of these devices include those manufactured and sold by Welch Allyn, Inc. of Skaneateles Falls, N.Y., among others. In optical versions of these devices, such as an otoscope or ophthalmoscope, a diagnostic handle retains a set of standard or rechargeable batteries in which an instrument head is attached to the top of the handle, the instrument head retaining the optics required to permit examination of a target of interest. Digital versions have also been manufactured in regard to at least some of these devices.

Still further certain examinations, such as those involving the eye, have only been possible using a dedicated and much more complex apparatus, such as a fundus camera that is used for purposes of conducting retinal imaging of the eye and further permitting the detection of other maladies, such as diabetic retinopathy and macular degeneration, given the field of view that is required and in which a patient is examined without having to administer eye drops in order to dilate the pupil for purposes of conducting an examination.

It is a general and ongoing need in the field to develop improved digitally based medical devices, including medical examination instruments.

SUMMARY

Therefore and according to one aspect, there is provided a hand held ophthalmic examination instrument comprising an illumination system for providing illuminating light, the illumination system directing the illuminating light toward a target of interest. The illumination system includes a first light source emitting the illuminating light in a narrow wavelength range of between about 550 nm and about 600 nm, a second light source for emitting a flash of white (broadband) light, wherein said illumination system directs both the illuminating light and the flash of the white light toward the target of interest, and at least one lens for directing light rays of the illuminating light and of the flash of white light in preselected directions toward the target of interest. The ophthalmic instrument further comprises an imaging system for directing the illuminating light as reflected from the target of interest to a viewing location, in which the imaging system includes: a digital imager at the viewing location for detecting and capturing a digital image of the target of interest, and a digital display electrically connected to the digital imager for displaying the captured digital image of the target of interest. The ophthalmic instrument further includes a memory for storing the captured digital image of the target of interest and a processor electrically connected to the memory, the illumination system, and the imaging system for controlling operation thereof.

According to one version, the hand held ophthalmic instrument comprises a converging lens for converging light rays of the illuminating light and of the flash of white light toward an apex. In one embodiment, the apex is situated at or near a pupil of an eye.

According to another version, the imaging system further includes a plurality of lenses forward of said viewing location and centered on an optical axis of the examination instrument, and wherein one of the plurality of lenses includes an optical focusing element capable of varying its thickness in response to an application of a focusing voltage thereto. More specifically, the optical focusing element can comprise a so-called "liquid lens", wherein the instrument can include an automatic focus control capable of varying the focusing voltage until a focused image of the target of interest is captured by the imager. At least one or a plurality of such lenses can further provide a system less prone to image jitter.

According to one version, the instrument includes a memory for storing at least two preset focusing voltages, wherein the at least two preset focusing voltages are alternately applied to the focusing element under control of the processor for alternating a focal length of the focusing element corresponding to the at least two focusing voltages such that the digital display alternately displays the target of interest as captured at the at least two alternating focal lengths. According to yet another version, the imaging system further includes a beam splitter for directing a portion of the illuminating light as reflected from the target of interest to a second viewing location, and a second digital imager at the second viewing location for detecting and capturing a second digital image of the target of interest. A second plurality of lenses is disposed forward of the second viewing location, wherein one of said second plurality of lenses includes a second focusing element capable of varying its thickness in response to an application of a second focusing voltage thereto, and wherein the digital display is electrically connected to the second digital imager for displaying the second digital image on a portion of the digital display.

The instrument preferably further comprises a DC power source for providing electric power to the illumination system and the imaging system. According to one version, the power source comprises at least one of a rechargeable DC power source such as a battery. According to another version, the rechargeable DC power source includes a super capacitor or an ultra capacitor.

The first light source can include an LED, a laser diode, or an incandescent bulb. According to one version, the first light source comprises means for varying the wavelength of light emitted by the first light source.

The second light source can according to at least one version, include a plurality of LEDs each separately illuminable and each emitting light having a different wavelength than another one of the LEDs. Alternatively, the second light source can include at least one of a white light LED, a white light laser diode, and a white light incandescent bulb.

In a preferred version, the instrument further comprises a fixation light source positioned at a preselected distance from the optical axis such that when a person directly views the fixation light source, a preselected area of the person's retina is visible to the imaging system. In another version, a plurality of fixation light sources are each positioned at a preselected distance from the optical axis, the plurality of fixation light sources arranged in a circular formation and each illuminable individually such that when a person directly views an illuminated one of the fixation light sources a preselected area of the person's retina, corresponding to a position in the circular formation of the illuminated one of the light sources, is visible to the imaging system.

The processor of the herein described instrument can comprise a program for stitching together into one continuous digital image, the preselected areas of the person's retina captured by the imaging system.

The digital display according to at least one version includes a size and location adjustable cursor box controlled by the processor in response to user input for selecting an area of the digital display corresponding to an area of the target of interest to be captured as a digital still image.

According to another version, the instrument can further comprise a microphone connected to the processor for capturing an audible voice command, wherein the processor is programmed to initiate capturing a digital image of the target of interest in response to the voice command.

According to another version, the instrument comprises means for controlling a property of the light emitted by the first or the second light source. These means can comprise an aperture wheel or an adjustable iris for controlling a width of a beam of light emitted by the first or the second light source. In another version, the width controlling means can comprise at least one filter positioned forward of the first or the second light source for filtering the light emitted by the first or the second light source. The at least one filter can comprise, for example, a color filter or a polarizing filter.

In at least one version, the instrument includes a communication interface for connecting the processor to an external processing system and for exchanging data between the processor and the external processing system. An indicator can be provided on the instrument or otherwise for indicating that a data exchange is in progress and status of the data transfer. The data exchanged between the processor and the external processing system can include software upgrades transmitted to the instrument as well as captured digital images transmitted to the external processing system. The communication interface can be at least one of a wireless communication interface or a wired communication interface. A wired communication interface can comprise at least one of a USB interface, a PCI interface, an ePCI interface, and an Ethernet interface. The wireless communication interface can comprise at least one of an IEEE 802.11 interface, a cellular interface, or another wireless standard compliant interface.

According to yet another version, the ophthalmic instrument further comprises a patient interface including an eye cup for coupling the examination instrument with the patient, and configured for contacting a region of the patient's face surrounding an eye of the patient. The eye cup according to at least one version is fabricated from a flexible material for conforming to the region of the patient's face surrounding the eye of the patient and includes flexible ribs for flexibly conforming to the region of the patient's face surrounding the eye of the patient. In a preferred version, the eye cup comprises an opening therethrough, wherein a pupil of the eye of the patient can be viewed from a position external to the examination instrument. Using the above, a distance between the pupil of the eye and the converging lens and the width of the beam of light emitted by the first or the second light source are both adjusted such that a region of a retina of the eye that is illuminated by the illuminating light comprises between about twenty degrees and about thirty five degrees.

According to yet another version, there is provided a method of performing an ophthalmic examination, the method comprising the steps of: illuminating a target of interest using amber light comprising a narrow wavelength range of between about 550 nm and about 600 nm; and following said step of illuminating, illuminating the target of interest using white (broadband) light; and simultaneously with said step of illuminating the target of interest using white light, capturing a digital still image of the target of interest.

According to at least one embodiment, the step of illuminating the target of interest using white light comprises the additional step of emitting the white light for less than about one-tenth of a second.

In one version, the step of simultaneously capturing the digital still image comprises the step of using an electronic digital imager and in which the displayed image is illuminated by the amber light. In one version, the method further comprises the step of automatically focusing the target of interest simultaneously with said step of illuminating the target of interest using the amber light. In one version, the latter step comprises the additional step of adjusting a focal range of a liquid lens, which can be done, for example, by the additional step of varying a voltage applied to the liquid lens.

In one preferred version, the target of interest is an eye and wherein the step of illuminating the target of interest using the amber light comprises the additional step of converging light rays of the amber light at an apex at or near a pupil of the eye. In one embodiment, the illuminating step is performed using an LED that emits the amber light. In another version, the LED can be a white LED wherein an amber filter is positioned in front of the LED.

Similarly and according to one version, the step of illuminating the target of interest using the white light comprises the additional step of activating an LED that emits the white light. In another embodiment a plurality of LEDs can be activated, emitting light of different colors for generating the white light.

In one embodiment, the step of capturing a digital still image of the target of interest comprises the additional step of adjusting a cursor box on the digital display around a portion of the target of interest as illuminated by the amber light. In another version, the above step can be carried out by detecting an audible command for electronically triggering the step of capturing the digital still image.

One advantage that is realized herein is that of enhanced imaging capability that can be commonly imparted to a suite of medical examination instruments and other types of medical devices, including monitors. The introduction of at least one optical focusing element, such as at least one liquid lens assembly, enables dynamic focusing which accelerates the overall examination process and overall ease of use of the device design.

Another advantage is that a plurality of different medical devices can interrelate with a common docking and charging station for purposes of charging and for data storage, retrieval and transmission.

Still another advantage is that an eye examination can be successfully provided with numerous features that have only previously been available in larger and far more complex and costly fundus cameras. Enhanced diagnostic capability is provided in a narrow (undilated) pupil.

Yet another advantage is that use of a variable focus lens assembly, such as a liquid lens, significantly reduces the incidence of image jitter. Other features can also be provided, such as inclusion of at least one positional sensor that simplifies the operation of the device and reduces the amount of direct user interaction.

Still another advantage is that of modularity of instruments, such as a suite of diagnostic or examination instruments is made possible.

These and other features and advantages will be readily apparent from the following Detailed Description, which should be read in conjunction with the accompanying drawings.

BRIEF DESCRIPTION OF THE DRAWINGS

FIG. 1A is a partial side elevational view, taken in section, of an exemplary medical device in accordance with a first embodiment;

FIG. 1F is a schematic view of the imaging system of the exemplary medical device of FIG. 1A;

FIG. 2A depicts a side elevational view of a variable focus lens assembly in accordance as used in the medical device of FIG. 1A;

FIG. 2B depicts a single variable focus lens assembly;

FIG. 2C depicts a multiple variable focus lens assembly;

FIGS. 3A-3B depict a pixel binning method;

FIG. 3C depicts a schematic circuit diagram for selectively performing a pixel binning method;

FIG. 5B is a front facing view of a medical device including a circular array of aiming/fixation lights;

FIG. 5C is the side elevational view of the medical device of FIG. 5B;

FIGS. 6A and 6B are schematic views of the optical system of a medical device illustrating a field of view control for reducing a distance between a patient's eye and the diagnostic instrument for increasing a field of view of the patient's retina;

DETAILED DESCRIPTION OF THE PREFERRED EMBODIMENTS

Figure 1B:
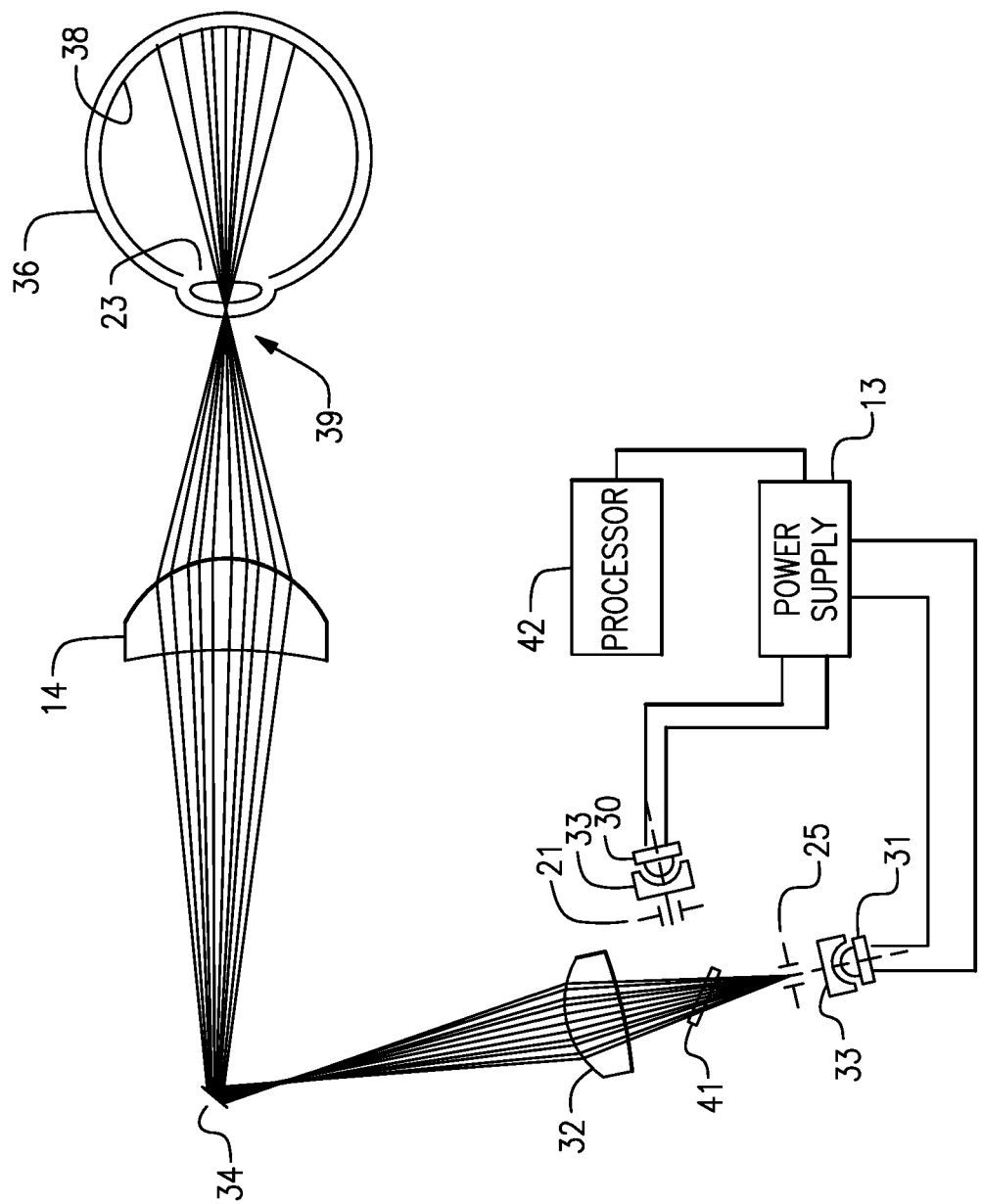
FIG. 1B is a partial schematic view of the illumination system of the exemplary medical device of FIG. 1A.

The following discussion includes numerous exemplary embodiments of medical devices, and more specifically medical examination instruments that permit digitized images of a medical target of interest to be captured, whether displayed locally at the instrument and/or remotely for purposes of examination. In order to provide a suitable frame of reference in regard to the accompanying drawings, certain terms are used throughout this description. These terms, such as "lateral", "above", "below", "distal", "proximal", "top", "bottom", "upper, "lower", "inner", "outer" and the like are not intended to narrow the scope of the herein described invention as further defined in accordance with the claims, except where so specifically indicated.

In spite of the numerous examples provided herein, it should be readily apparent that many other variations and modifications can be contemplated by one of sufficient skill, including but not limited to alternatives involving the specific instrument and overall functionality as well as attendant features.

As used herein, the terms "medical diagnostic device or "medical instrument" and "medical examination device or instrument" are used interchangeably and pertain to a medical field instrument, such as but not limited to an otoscope, an ophthalmoscope, a skin microscope, an endoscope, a colposcope, a rhinoscope, a laryngoscope, an anoscope and the like in which diagnostic or examination data can be obtained through imagery of the patient. The concepts as related herein are intended to be applicable to any such device, including but not limited to monitors.

As used herein, the term "electronic imager" refers to an electronic charge coupled device (CCD) array, a CMOS photodiode array or similar devices that can be used to capture a digital image.

As used herein, the term "imaging" refers to capturing a digital image of a target of interest using the electronic imager.

As used herein, the term "optical focusing element" can refer to a variable focus lens assembly, such as at least one liquid lens assembly wherein a thickness of the lens varies, and thereby its focal plane, according to a voltage level applied thereto.

As used herein, the term "illuminating system" refers to light sources and components to direct light beams therefrom to illuminate a target of interest.

As used herein, the term "primary axis" refers to the center axis of the housing extending through each of the distal and proximal ends of the medical device.

As used herein, the term "processor" refers to a general purpose processor, an embedded processor, or controller coupled to a digital memory system comprising instructions retrieved and executed by the processor for controlling operation of all electronic components of the medical diagnostic instrument in response to user inputs received from user interface input means and from data received from the electronic components that indicate status of the components.

As to the discussion that follows, a generic medical device is first discussed prior to descriptions of more specific exemplary device embodiments. In general and first referring to FIG. 9, a generalized schematic diagram of a medical device is herein described. First, the medical device 1000 includes a housing 1004 fabricated from common metallic alloys or thermoplastic resins and defined by an interior 1008, which is appropriately sized to retain a number of components or in which the housing 1004 is configured to receive a peripheral device, shown in phantom as 1090 and as discussed infra. The housing 1004 is suitably shaped for portable use, wherein the housing 1004 can include an integral handle 1012 according to at least version in order to facilitate single-handed operation.

The housing 1004 is defined by a distal end 1016 that retains a patient interface (shown schematically as 1020) and an opposing proximal end 1024. The patient interface 1020 can be integrated with the housing 1004 or separably attached thereto, as discussed in the various exemplary embodiments which follow, and in which the interface directly contacts an area of a patient in at least one version. As noted, the handle 1012 extending from the lower portion of the housing 1004 enables the device 1000 to be compactly held and operated using only a single hand of a user (not shown) and can further retain a portable power supply 1018, as discussed herein, although other portable configurations, with or without handles, are possible.

The portable power supply 1018 can include at least one standard battery such as a lithium-ion battery or a rechargeable battery. As described in U.S. Pat. No. 9,153,994, entitled Motion Sensitive and Capacitor Powered Handheld Device, issued Oct. 6, 2015, and U.S. Pat. No. 8,890,489, entitled Capacitive Power Supply for Handheld Device, issued Nov. 18, 2014, which are hereby incorporated herein by reference in their entireties, power supplies comprising high energy density capacitors, e.g. super capacitors or ultra-capacitors, may be utilized as the power supply in the medical diagnostic imaging instrument 10. Such power supplies allow fast charging times sufficient to store enough electrical energy to power the instrument for several hours and therefore can enable limited numbers of operation with a very short charge time, or a hybrid combination of the above battery types can be provided.

An optical system 1030 (shown in phantom) is retained within the interior of the housing 1004 and includes a plurality of optical components or elements commonly aligned along an imaging axis 1040 of the device 1000 in order to permit an image of a target of interest 1044 to be suitably directed onto an electronic imager 1050, such as a CCD, a CMOS or other suitable component. According to this embodiment, the imaging axis 1040 is coincident with the primary axis of the medical device 1000 although this positioning can be suitably altered, as discussed infra.

The overall constituency of the optical elements that are provided in the optical system 1030 will obviously vary between types of medical devices including various examination instruments, as discussed herein for purposes of acquiring a suitable image of the intended target of interest 1044. In addition, the optical system 1030 can further include a focusing mechanism in which at least one optical element or the imager 1050 is moved in relation to each other. According to at least one version, at least one optical focusing element, such as at least one liquid lens assembly, is arranged along the imaging axis 1030 of the device 1000 and as further discussed in subsequent embodiments. The addition of the latter assembly enables dynamic "on the fly" focusing automatically with no moving parts and in which jitter is effectively reduced.

The device can also include an illumination system 1060 that comprises at least one light source 1066 capable of producing adequate light along a defined illumination axis 1070 of the device 1000 towards the target of interest and to enable imaging by the electronic imager 1050. In at least one version, the illumination system further provides means to allowing aiming the instrument for purposes of imaging a specific medical target of interest, as discussed herein, such as portions of the eye.

The light source 1066 can be an incandescent bulb, an LED, a laser diode, or other suitable source that, along with aligned illumination optics produces an adequate beam of light incident on the target of interest. According to at least one embodiment, this source 1066 can be suitably be configured as discussed herein to provide varying wavelengths of light to the target to provide standard, spectral, polarization and/or other forms of digital imaging depending on the application (examination) being performed. In one version, the light source can comprise an array of LEDs, including infrared and near infrared. In another version, at least one filter and/or polarization element can be provided in conjunction with either the imaging and/or illumination systems of the device 1000 to alter the wavelength of emitted light and/or to reduce the incidence of glare. According to another version, the illumination system can be optional, for example, when using IR detection such s from the skin of a subject.

The medical device 1000 further includes a display 1072, which, according to one version, is integrated with the instrument housing 1004 and connected to a processor 1076 for purposes of processing images taken by the electronic imager 1050 for presentation. Preferably, the display 1072 can be aligned with the primary axis of the device 1000 to provide a compact and convenient overall design, although other suitable arrangements can also be utilized and as illustrated herein. In another version, the display itself can also be optional in the instance in which the electronic imager 1050 and processor combine to simply capture and store a plurality of images for later transmission to a remote site.

A user interface (UI) 1080 to enable operation, as needed, includes at least one actuable element 1084, such as a button or switch, disposed on the housing 1004 and interconnected to the processor 1076. In the current embodiment, the user interface 1080 is provided along one side of the handle 1012 of the device 1000, but could also be disposed, for example at or near the display 1072. In an effort to reduce the overall complexity of the UI 1080 and also to minimize the risk of image jitter caused by user interaction, at least one positional sensor 1086 can be disposed on or proximate the housing 1004 to provide a signal that is transmitted to the contained processor 1076. For example, the positional sensor 1086 can comprise at least one accelerometer, such as a three-axis accelerometer. In one embodiment, the accelerometer can detect and produce a signal when the housing 1004 is being picked up, as would be the case in actual use or in the instance in which a signal has not been detected for a predetermined time interval indicative of inactivity. In the former example, the signal from the accelerometer causes the device 1000 to automatically power up while the latter can cause the instrument to assume a dormant or "sleep" mode of operation. According to yet another example, the positional sensor 1086 can comprise an attitude sensor, such as a gyroscopic sensor, that senses azimuthal or other positional changes in the instrument housing 1004. According to yet another example, a signal can be produced by a user that can be detected by the positional sensor 1086, such as by tapping one side of the display 1072, which can be indicative of either a left or a right image being taken by the medical device 1000.

According to another version, and also to prevent unnecessary movement a voice command feature can be provided. A microphone 15 (FIG. 1A) built into the instrument housing 29 detects the voice of the operator of the instrument. A voice recognition program stored in the processor 24 can therefore control certain features of operation, and avoiding the overuse of user actuated controls. According to one embodiment, the use of voice commands can control the exposure step for imager 20. Advantageously, the voice command image capture step avoids the requirement that an operator press a button or otherwise make physical contact with the medical diagnostic imaging instrument 10, thereby avoiding unnecessary movement of the instrument during digital image capture.

As discussed herein according to at least one other version, the electronic imager 1050, display 1072, processor 1076 (or at least portions thereof) and optionally at least a portion of the illumination system 1060 can be separately defined within a peripheral device 1090, such as a smart phone, a tablet computer, an iPad or any other suitable compact device that includes a portable camera, which is releasably attached to the housing 1004 and in which the electronic imager of the peripheral device is aligned with the imaging axis of the device 1000. Application software that is resident within the peripheral device 1090 enables use of same with the medical device 1000 in which enhanced capabilities of the peripheral device 1090 itself creates versatility, as well as additional processing power. In terms of the smart phone, for example, the optical system 1030 of the device 1000 can be augmented such that the imaging axis 1040 is aligned with the electronic imager (not shown) of the attached peripheral device 1090, while enabling the peripheral device to be disposed substantially along the primary axis of the device 1000, providing compactness of design but without impacting functionality.

Figure 8:
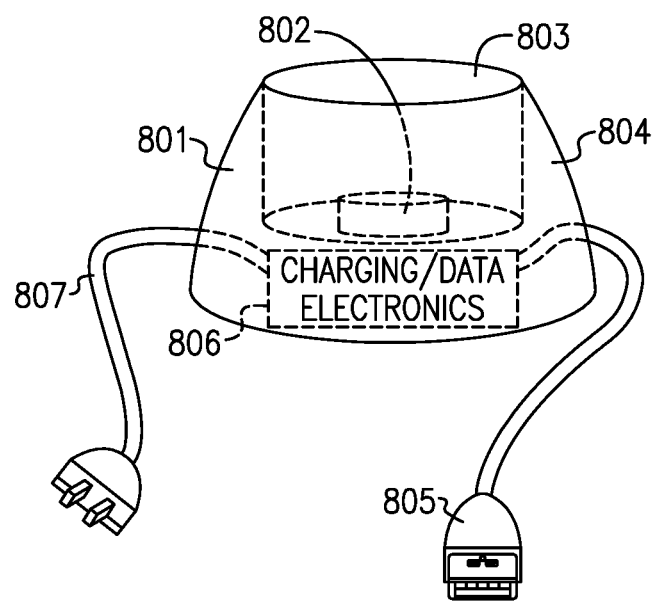
FIG. 8 depicts an exemplary docking station for a medical device.

Otherwise and in a dedicated device 1000, the processor 1076 can be arranged within the housing 1004 and connected to the electronic imager 1050, the display 1070 and the illumination system 1060, the processor 1076 having resident software for operating the medical device 1000 based on inputs from the user interface 1080 and embedded instructions. The retained power source 1018 can be recharged using a docking station, shown schematically as 1094, configured to receive at least one said medical device 1000 and in which data transfer can also be initiated either automatically through attachment or selectively using wired or wireless transmission means (arrows 1096, 1097). The docking station 1094 can also be configured to serve as a recharging port for the contained power supply. Another example of a station is shown in FIG. 8 and described in greater detail below.

Advantageously, the present invention provides a medical device that utilizes an electrically controllable focusing system that is simple, compact, provides the desired dynamic range, has few moving parts, consumes a minimum of electrical power, and can be incorporated into existing instrument designs. With the preceding generic description, the following embodiments present certain embodiments that are specific to various exemplary medical examination instruments and more specifically ophthalmoscopes, otoscopes, skin measuring microscopes and colposcopes. It will be understood, however, based on the above generic description that the concepts discussed herein are equally applicable to other medical devices, such as but not limited to endoscopes, retinoscopes, rhinoscopes, larygnoscopes, anoscopes, and the like.

An ophthalmic instrument is herein next described. Referring first to FIGS. 1A-1D and more specifically to FIG. 1A, a cross-sectional view is provided of the ophthalmic instrument 10 having an illumination system 11 and an imaging system 12. FIG. 1B is a schematic diagram, shown in isolation, of the illumination system 11 of the instrument 10. FIG. 1F is a schematic diagram, shown in isolation, of the imaging system 12 of the instrument 10 for use in illuminating and forming an image of a target such as a portion of a patient's eye, for example, the retina. With regard to the illumination system 11, there are included separately controllable light sources 30, 31, a condensing lens 32 and a mirror 34 each disposed along a defined illumination axis 35. The light sources 30, 31 can be any generic light source, such as a filament based lamp, a metal halide lamp, a Xenon lamp, the end face of a fiber optic cable, a laser diode, or a single or multiple LED array.

Figure 1C:
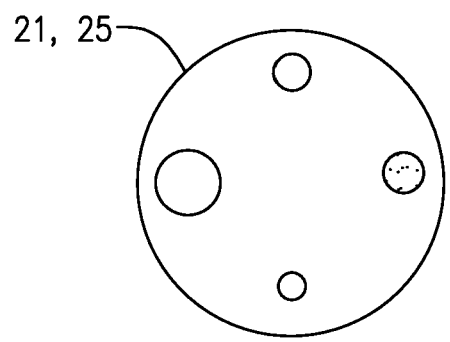
FIG. 1C depicts an enlarged view of an exemplary means for varying aperture of light source of the medical device of FIG. 1B.

In one embodiment, the light sources 30, 31 comprise single or multiple LED elements which can be illuminated individually or simultaneously. Exemplary LED light sources comprise a source of white light such as an RGB LED having wavelengths of the red (R), the green (G), and the Blue (B) colors of the white spectrum. In one embodiment, the light sources 30, 31 comprise a filter 33, such as an infrared filter for permitting light wavelengths of about 780-820 nm to pass therethrough or an amber filter to permit light wavelengths of about 580-610 nm to pass therethrough for reasons discussed herein. Either or both light sources 30, 31 may include a filter positioned forward (i.e., distal) of the light source. Light sources 30, 31 further comprise aperture wheels 21, 25, respectively, to direct light, represented by light cones 26, 27, respectively, along an illumination axis 35. An example of a mechanically operable aperture wheel is illustrated in FIG. 1C, wherein apertures of various sizes can be rotated into an aligned position forward of light sources 30, 31 and along the illumination axis 35. A smaller aperture size allows less light to pass therethrough but the light is constrained into a narrower beam. A larger aperture size can be used to allow more light along the illumination path such as, for example, if a larger region of a retina is to be illuminated. Alternatively, other means for varying the amount of incident light can be utilized; for example, an adjustable iris (not shown).

A condenser lens 32, centered on the illumination axis 35, converges light from the light sources 30, 31 onto the mirror 34, which reflects the illuminating light along an imaging axis 22 to an objective lens 14, which causes the light to converge at an apex 39 at or near the cornea 23 of a patient's eye 36 and diverges inside the eye 36 of the patient to illuminate a wide area of the retina 38. Light can be selectively emitted from the second light source 30, under control of a processor 42 using a contained power supply 13, and reflected off a beam splitter 41 disposed along the illumination axis 35 through the converging lens 32 to the mirror 34. Light emitted from the light source 31 travels through the beam splitter 41 along illumination axis 35 through the converging lens 32 to the mirror 34, which reflects the illuminating light parallel to the imaging axis 22 to the objective lens 14, as before.

Imaging system 12 includes at least one objective lens 14 (which also forms part of the illumination system), an imaging lens 16, a variable focus liquid lens assembly 18, and an electronic imager 20 each spaced and aligned along the imaging axis 22. The lens assembly 18 is controlled by the contained processor 42 using a variable voltage control 24 or other suitable means. The electronic imager 20 may comprise any known image sensor, such as a CCD or CMOS imager. During examination of a patient, the imaging axis 22 is approximately coincident with the optical axis of a patient's pupil 23. In all references herein, the terms "lens" and "lens assembly" can refer to a single optical element or a plurality of optical elements functioning together. Light reflected from the retina 38 of a subject is transmitted along the imaging axis 22 by the objective lens 14, through an image plane 28, the focusing lens assembly 18 and the imaging lens 16 to the electronic imager 20. The imager 20 produces an electronic (digital) image, which is displayed on display 40 after the signal has been processed by the processor 42. The processor 42 can be programmed to control the electronic imager 20 during exposure and to capture and store image data generated by and received from the imager 20. The processor 42 can execute autofocus software wherein an image displayed on the display 40 is automatically focused through a lens voltage control 24 and the focusing lens assembly 18.

The processor 42 detects the image state of focus and drives voltage to the liquid lens 18 to obtain the sharpest image. The response time of the processor 42 in transmitting voltage control signals to the focusing lens assembly is sufficiently rapid to reduce, to a certain extent, shaking or jitter effects during image capture, and so serves to significantly minimize the incidence of jitter. As described herein, the processor 42 is disposed within the confines of the instrument housing 29, but could alternatively be located external to the instrument 10. If located externally, the processor 42 can communicate with the imager 20 either through wired or wireless communication channels (not shown in this embodiment). The components of the instrument 10 are preferably contained in the housing 29 that can be maintained by gripping a handle portion thereof and in which the instrument is configured for single handed operation. Alternatively, the components of the instrument 10 can be contained in a housing fixedly supported on a table, floor or other surface.

Figure 18:
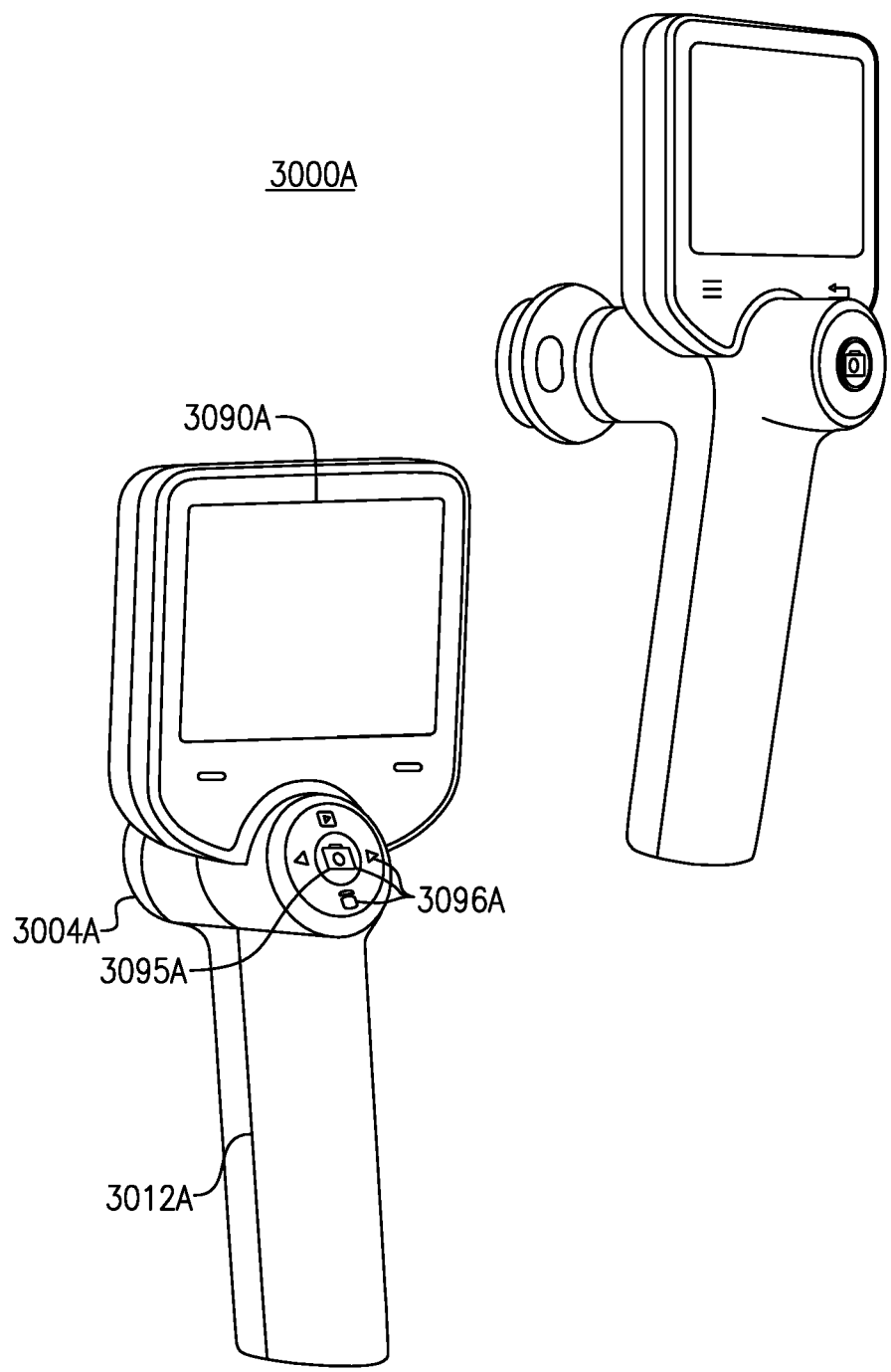
FIG. 18 is a rear perspective view of the medical device of FIG. 17 alongside a second type of medical device.
Figure 19:
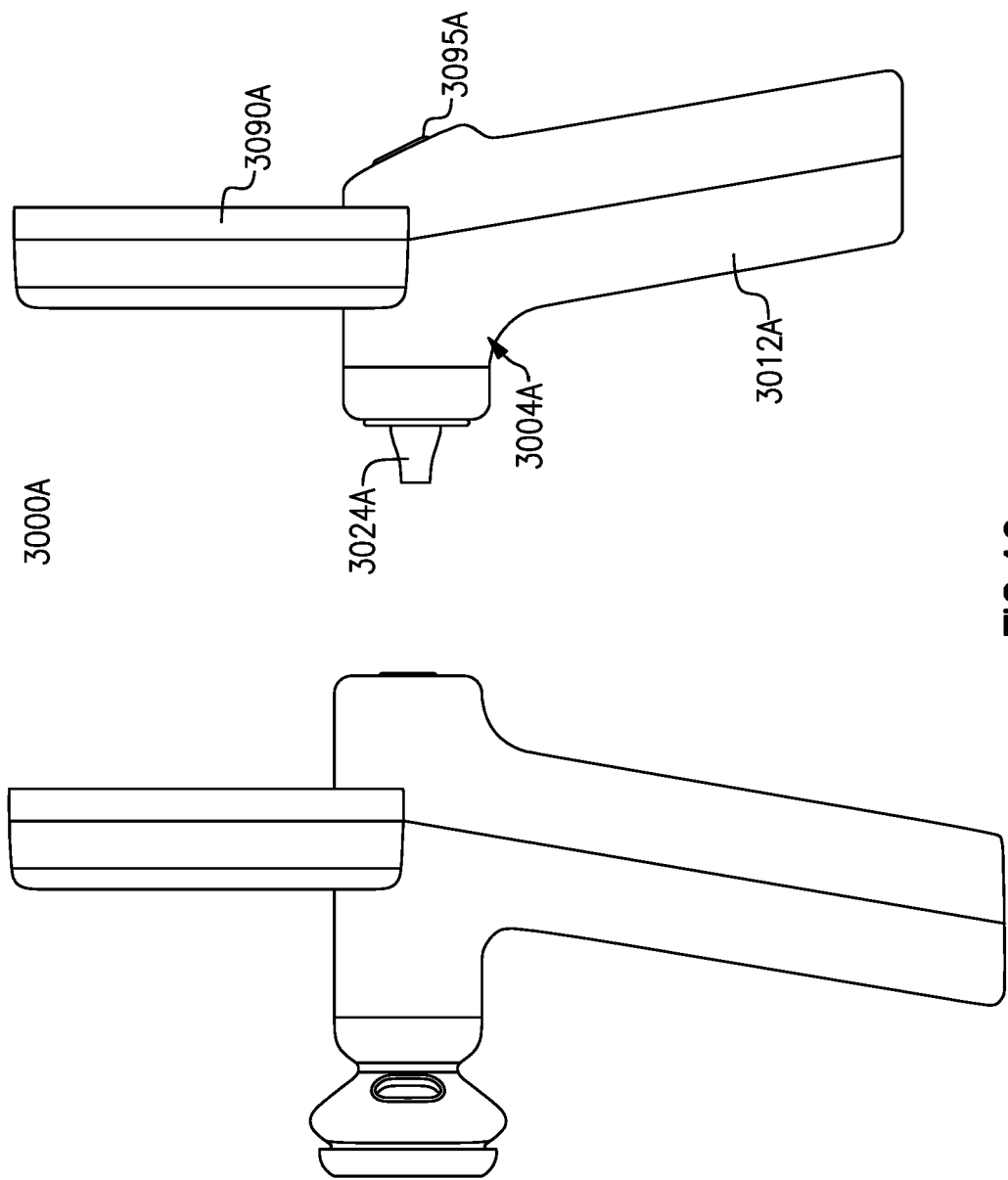
FIG. 19 is a side elevational view of the medical devices depicted in FIG. 18.

As shown in FIG. 1F, the image of a portion of the eye reflected along the imaging axis 22 is transmitted using the optical components of the imaging system 12 to the electronic imager 20, which is also appropriately aligned (i.e., centered) on the imaging axis 22. The display 40 can be suitably positioned for viewing by the user. In one version, the display 40 can be aligned along the imaging axis 22 such as on the housing 29, or alternatively, the display can be disposed away from the imaging axis 22 such as shown in FIG. 18, wherein the display screen 3090A is positioned off of, and above, the imaging axis 22. The electronic imager 20 produces an electronic image for display on the display 40 and can be viewed in real time thereon by the caregiver.

FIG. 2A is a diagrammatic view of a preferred variable focus liquid lens 18 that is incorporated within the imaging system 12 of the herein described ophthalmic instrument 10 and aligned along the imaging axis 22. As shown and according to this exemplary embodiment, the variable focus liquid lens assembly 18 includes a housing 61 that incorporates a pair of parallel transparent windows 62 and 63, a first electrode 64 having a frusto-conical opening 65, an insulating layer 66 disposed on the first electrode 64, a second electrode 67, an insulator 68, a drop of insulating liquid 69 located on the conical insulating layer 66 and on the window 63, and an electrically conductive liquid 70 filling the remainder of the housing 61. The filled conductive liquid 70 is in electrical contact with the second electrode 67 while the insulating liquid 69 and the conductive liquid 70 are in contact along a meniscus region represented by solid line 71. The insulating liquid 69 and conductive liquid 70 are both transparent, are immiscible, have different optical indexes, and have substantially the same density. Conductive liquid 69 can, for example, be water mixed with salts and insulative liquid 70 can be oil. In one embodiment, the lens assembly 18 includes one or more electrically controllable variable focus liquid lenses. As shown in FIG. 2B, the lens assembly 18 includes one variable focus liquid lens 50, or, as shown in FIG. 2C, the focusing lens assembly 18 may alternatively include first and second spaced variable focus liquid lenses 51 and 52 with a controllable variable iris 54 located between the lenses 51 and 52. The variable iris 54 controls the amount of light passing through the liquid lens assembly 18 comprising multiple liquid lenses 51, 52.

In operation and when no voltage is applied, the system is said to be at rest. In this configuration, the drop of insulating liquid 69 naturally takes the shape of the solid line designated by reference curve 71. An axis 72 is perpendicular to the window 62 and passes through the center of the curve 71. At rest, the drop of insulating liquid 69 is centered about an axis 72, which is perpendicular to the window 62 and passes through the center of the reference curve 71. This latter axis 72 constitutes the optical axis of the lens.

Applying a non-zero voltage V from the variable voltage control 24 between the first electrode 64 and the second electrode 67 creates an electrical field localized in the region surrounding the electrodes. As a consequence, the conductive liquid 70 deforms the insulating liquid drop 69 and the reference curve 71 resultantly assumes the shape designated by the dashed line 74. This results in a variation of the focal length of the liquid lens. A range of applied voltages will result in a range of various radii of curvature for the dashed line 74 and therefore, a corresponding range of optical powers and focal lengths for the liquid lens.

One embodiment of an ophthalmoscope comprising the liquid lens 18, as described above, includes use of the liquid lens in assisting to align the imaging axis of the ophthalmoscope with a pupil of the patient. Under control of a caregiver who operates a toggle switch, or initiates a toggle function, in the ophthalmoscope's user interface, the liquid lens 18 can be switched between at least two focal lengths while the caregiver aligns the ophthalmoscope with the patient's pupil. One of the focal lengths is preselected for an overall view of the patient's eye (distal focal length) so that the caregiver can determine the spatial orientation of the ophthalmoscope as the caregiver advances the ophthalmoscope toward the patient's eye. Another of the preselected focal lengths comprises a standard, or caregiver preferred, focal length (near field focal length) used for examining a portion of the eye of the patient. Because the focal length of the liquid lens is controlled by the voltage applied thereto, as explained above, each preselected focal length corresponds to an applied voltage level, which level can be stored in memory as voltage level data to be accessed by the ophthalmoscope processor when the toggle function is selected by the caregiver. The voltage levels as applied are alternated according to the voltage level data which rapidly adjusts the liquid lens' focal length. The digital images generated as between the two focal lengths can be alternately displayed on the display 40 as the liquid lens is toggled and the ophthalmoscope is moved into position for examining an eye of the patient. The speed at which the toggle switch alternates between views may be preset, or controlled by the caregiver.

Another useful application of the toggling function includes a split screen display, or a picture-in-picture display, to simultaneously display the images as generated by the two preselected focal lengths. In the present ophthalmic embodiment in which one imager is used, one of the toggled images can be captured and displayed as a still image while the other image is simultaneously displayed as a live motion image. Thus, the toggling function serves to alternate between displaying one of the near field or distal focal length image as a digital still image while the other is displayed in live motion, and vice versa. In an ophthalmic or other embodiment using two imagers, each imager can independently and simultaneously transmit live motion images to be simultaneously displayed on display screen 40 as split screen or picture-in-picture live motion images. In this embodiment, the imagers may each implement a liquid lens assembly 18, in which each assembly is set at a different one of the preselected focal lengths so that the near field and distal focal length live motion images are simultaneously displayed on display screen 40. To generate two parallel imaging axes for the two imager embodiment herein described, a beam splitter can be disposed in the optical axis of the ophthalmoscope, or alternatively a collimation lens together with two mirrors can be used to generate parallel imaging axes each directed to one of the imagers. It should be noted that the foregoing arrangements are equally applicable in other instrument designs as used for other applications.

Figure 1D:
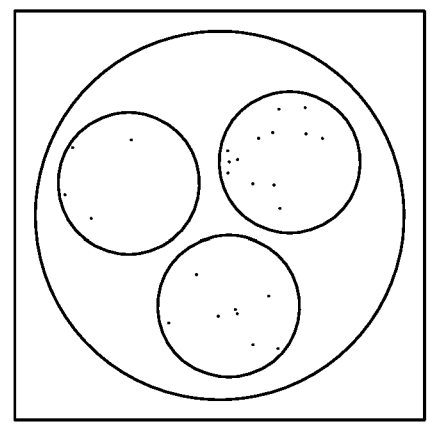
FIG. 1D is a front facing view of an LED die having multiple emitters.
Figure 1E:
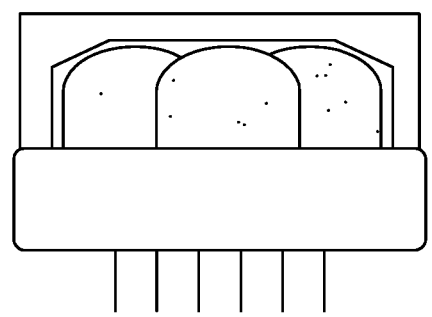
FIG. 1E is a side view of the LED die of FIG. 1D.

Light sources 30, 31 may be fitted with a filter 33 for providing light at selected wavelengths, depending on the filter that is utilized. For example, an infrared filter or an amber colored filter may be implemented as desired. In the present ophthalmic embodiment, an amber color filter 33 is utilized to provide illuminating light for observing a portion of an eye of a patient without causing an undue reaction in the patient due to light sensitivity, such as constriction of the pupil. The use of this filter therefore allows greater visibility of interior regions of the eye, such as the retina, without requiring dilation using eye drops, which is highly advantageous. Light in the amber wavelength range of about 590 nm allows the pupil to remain open while allowing a caregiver to observe desired interior portions of the eye. The caregiver can opt to capture a digital still image of the portion of the eye being examined, as desired. At the moment that a desired portion of the eye is in view on the display, the still digital image capture procedure may be initiated by manual or voice command, as described herein, under control of the processor 42 wherein a broadband white light source, such as provided by the light sources 30, 31 can be flashed and a digital image of the desired portion of the eye is captured while the eye is so illuminated. In this example, it may be preferable to modify the light source 30 to emit an amber wavelength light while the light source 31 is modified to emit white light. In another embodiment, the light sources comprise LEDs, without filters, whose emission spectra comprise desired wavelengths or illuminating light such as RGB LEDs for providing white light, and appropriately doped LEDs for generating amber colored light, for example. Such an arrangement of LEDs is shown in FIGS. 1D-1E wherein a width of each of the LEDs is about 1 mm or less. In yet another embodiment, the imager 20 may be sufficiently sensitive, or an environment, wherein an examination is taking place using the ophthalmic instrument 10, may provide sufficient natural light, to capture digital images without requiring an activation of illumination system 11. For example, if imager 20 is designed for detecting and capturing thermal images, then illumination system 11 may not require activation during image capture. In fact and in this latter example, the use of an illumination system can be made optional since infrared signals from a medical target would not require the incidence of light.

In another embodiment, each of the herein described light sources 30 and 31 can comprise a plurality of multi-color light sources, such as multiple LEDs, each emitting a different wavelength of light. Such LED light sources may be separately illuminable in order to provide illuminating light of various colors. Similar to the description above for using an amber colored light to illuminate a portion of an eye, and prior to capturing a digital image thereof, the multi-color light sources can be used to capture multiple digital images of a body part under various illumination conditions, such as illumination under light having different wavelengths. A series of exposures can be programmed to occur in a short duration with each exposure occurring under illuminating light having a different wavelength under programmed control of processor 42. Each exposure may be programmed to occur under several capture settings. For example, one or more exposures can each be programmed to be associated with a particular color of illuminating light, f-stop, exposure speed, and diopter setting. Each combination of settings be programmed to occur upon each exposure such that the eye (or other medical target) can be imaged under various illuminations and at various depths using optimal light conditions known to enable ideal image detail. For example and regarding a captured image of a relevant portion of the eye, the ratio of diameters of artery (A) to vein (V) provides useful information relating to hypertension.

Figure 20:
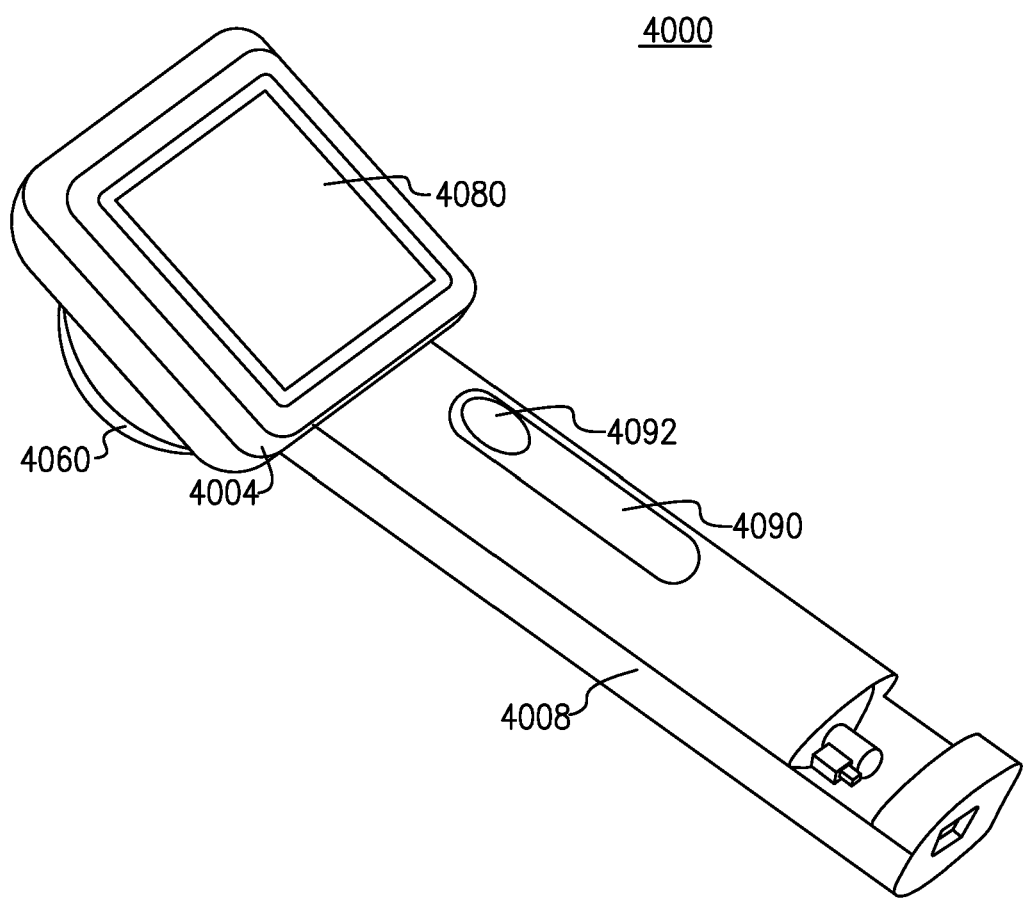
FIG. 20 is a rear perspective view of a portion of a medical device made in accordance with another exemplary embodiment.
Figure 21:
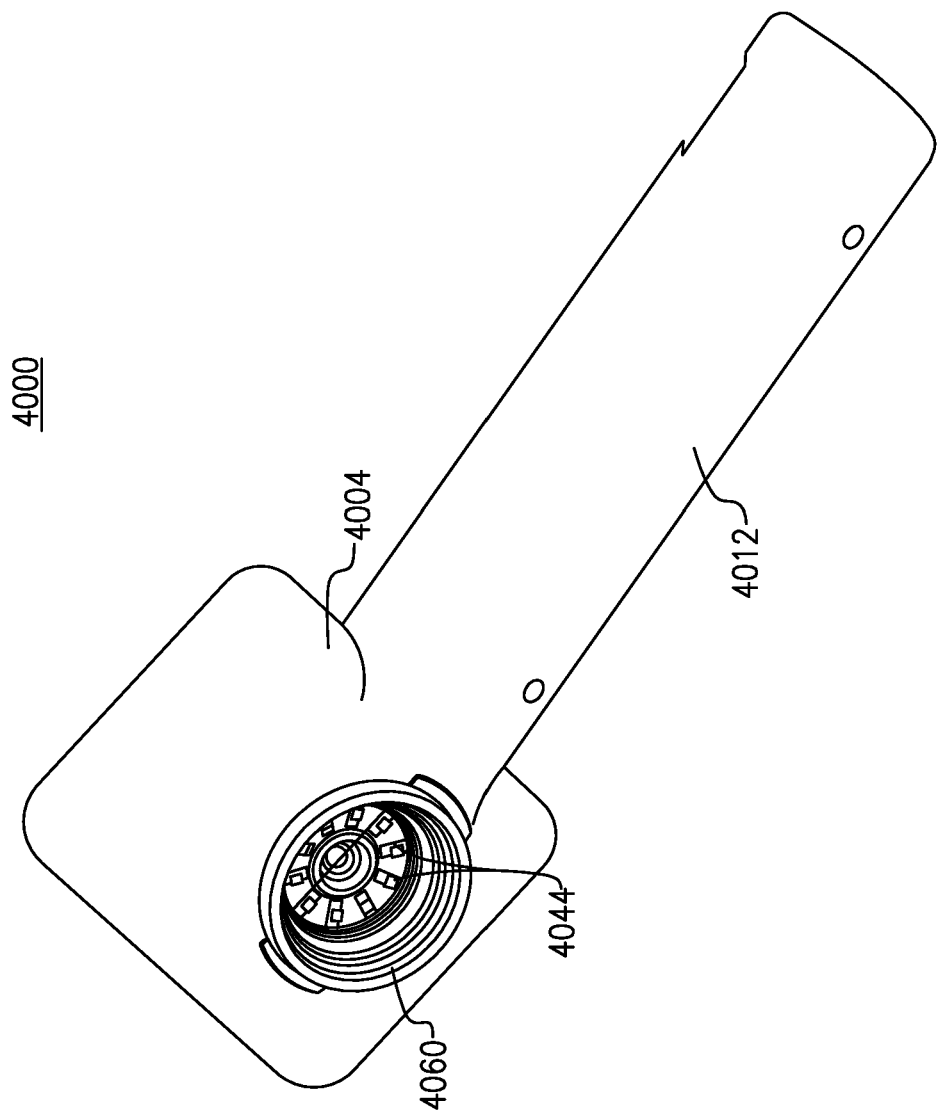
FIG. 21 is a front perspective view of the medical device of FIG. 20.
Figure 22:
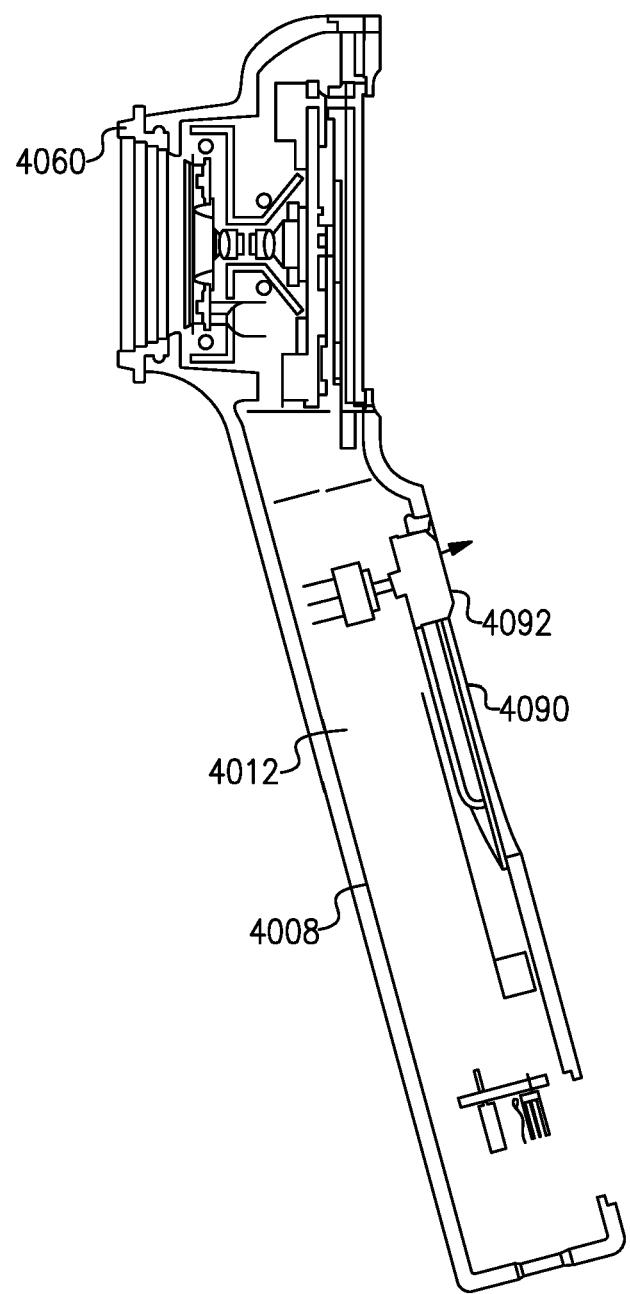
FIG. 22 is a side elevational view, taken in section, of the medical device of FIGS. 20 and 21.
Figure 23:
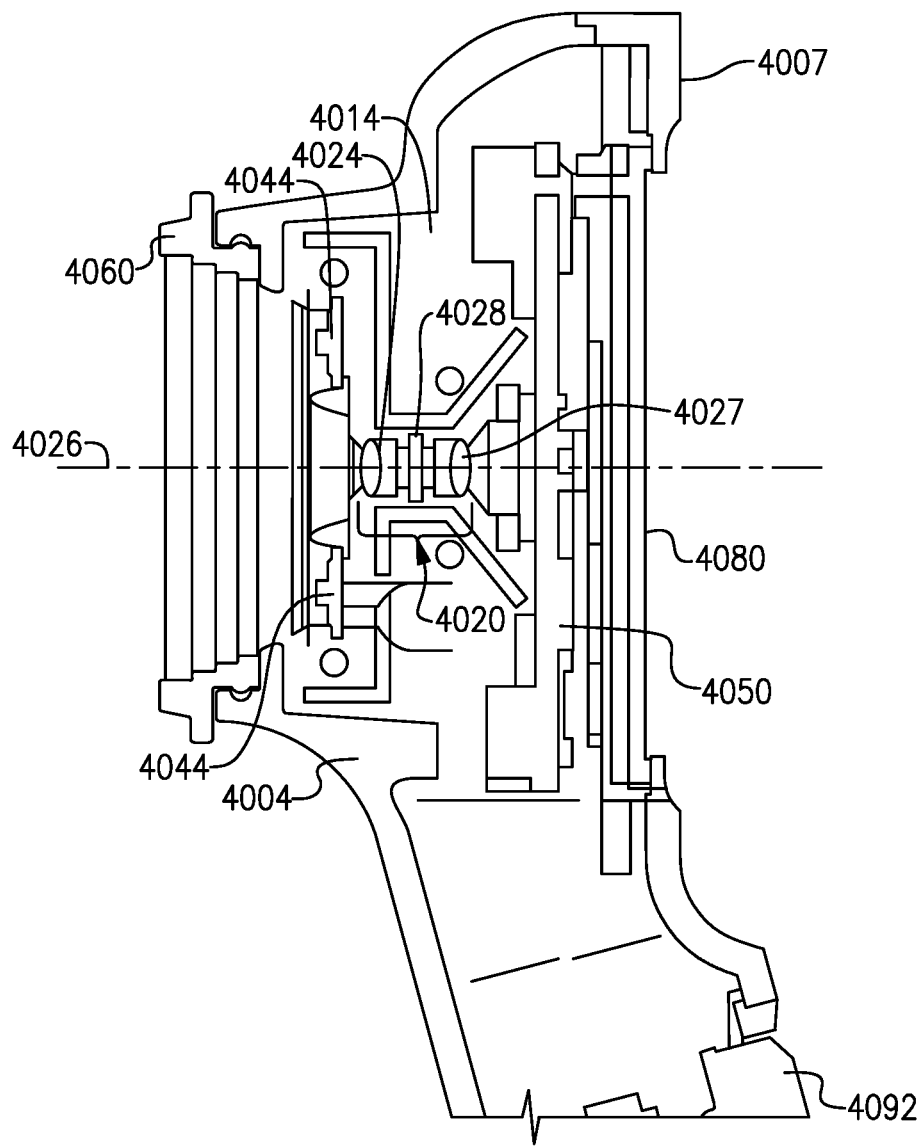
FIG. 23 is an enlarged section view of the medical device of FIGS. 20-22.

FIG. 3A illustrates a portion of the electronic imager 20 comprising a plurality of photodetectors (pixels) in the form of photodiodes for capturing image data. Each pixel comprises an image area for capturing light energy of a certain wavelength, e.g., green (G), red (R), and blue (B). The density of pixels arranged in an area of the imager 20 determines the resolution of the imager 20. The amount of light energy captured by each pixel determines a brightness of the captured image, while the resolution of pixels determines the sharpness of the image. A tradeoff occurs between brightness and sharpness of a captured digital image because the smaller the pixel size (area), the greater the digital image's resolution and the lower its brightness. Binning is a process (i.e., an algorithm) that can be designed to take advantage of these pixel properties, as desired. For example and under low light conditions, it may be preferable to increase an amount of brightness captured by the imager 20 even though resolution may be decreased thereby. In another example, if an electronic display screen, such as display screen 40 (or display screen 3090 of FIG. 14, or 3090A of FIG. 17-19, or 4080 of FIG. 20) is not capable of displaying a high resolution digital image, then the resolution can be decreased during an image capture step because it will not incur a cost as far as resolution display is concerned. As represented in the schematic circuit of FIG. 3C, each pixel 301 of the imager 20 transmits image capture data to an image processor during full resolution processing of captured image data. In this processing mode, maximum digital image resolution is obtained and can be displayed on an electronic image display having sufficient resolution. In a second mode of operation, all the pixels in the imager 20 are logically grouped into four adjacent pixels each 302 and are selectively connected to a summer circuit 304, under processor control, wherein the combined light energy captured by each group of four adjacent pixels is summed together. The sum is used to represent the value of a virtual quad-pixel 302, as shown in FIG. 3B, having about four times the size of one pixel in full resolution mode. This virtual quad-pixel captures more total light energy for increased brightness, but generates one-fourth the resolution as compared to a full resolution mode. Each group of four adjacent pixels consists of two green pixels, one red pixel, and one blue pixel, as defined by the familiar Bayer pattern utilized in many commercial image sensor arrays. The processor may be programmed to switch between full resolution mode and an increased brightness mode, as desired. Using this algorithm, more light energy is captured in each quad-pixel to represent one of a plurality of virtual re-sized imager pixels, thereby increasing overall visible image brightness, albeit with lower resolution, after processing.

Figure 4A:
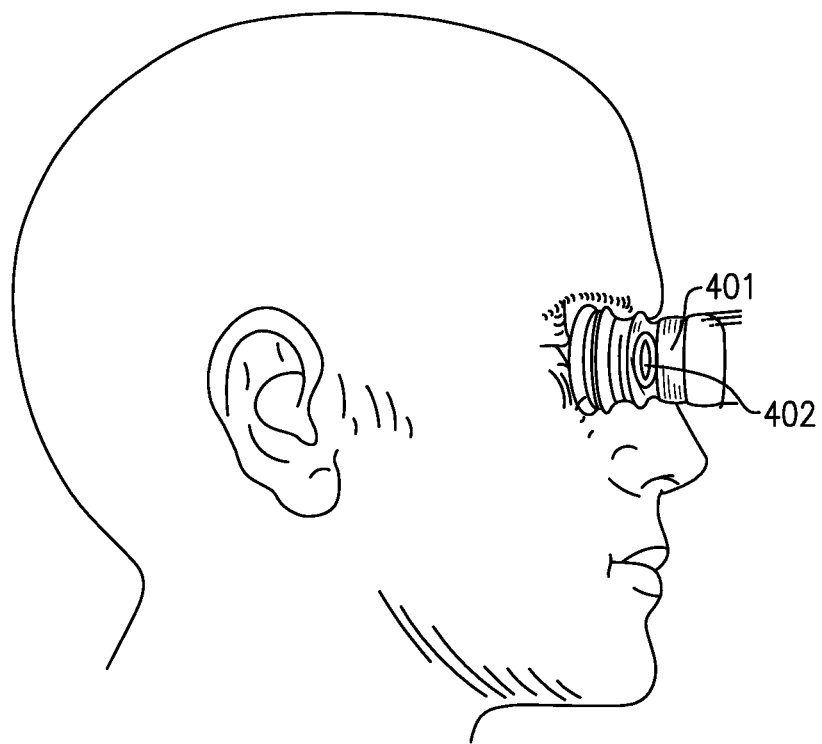
FIG. 4A depicts the engagement of the patient interface of the medical device of FIG. 1A.
Figure 4B:
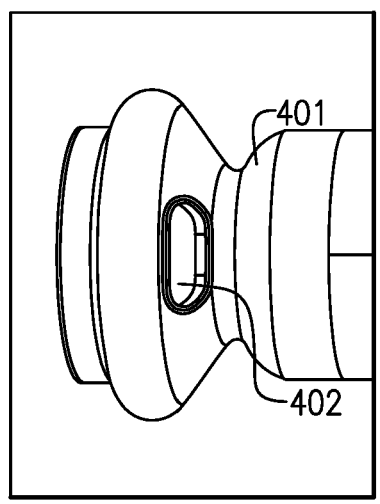
FIG. 4B is an enlarged view of a patient interface, including an observation slot.

With reference to FIG. 4, there is illustrated an eyecup portion 401 of the herein described ophthalmic instrument. According to this embodiment, the eyecup portion 401 may made of biodegradable and/or recyclable material or may be made from a biodegradable material or treatable with an additive, if made from polyethylene and polypropylene, such as Green Solutions PPI BD-0301 or Oxo-Degrader, among others, that degrades the interface within a prescribed time period. The eyecup portion 401 is modified to include a slot 402 that is angularly provided relative to a primary axis of the eyecup portion to permit a caregiver to observe a location of the patient's pupil with respect to the illuminating light emitted by the ophthalmoscope 10. By observing a patient's eye through the eyecup slot 402, the caregiver can position the illuminating light emitted by ophthalmoscope 10 so that the illuminating light is properly directed to a portion of the eye desired for viewing by the caregiver. After the caregiver confirms that the illuminating light is directed at the correct portion of the eye, such as the pupil, the caregiver can be assured that the image appearing on the display is correct and thereafter orient the ophthalmoscope using the display.

Figure 5A:
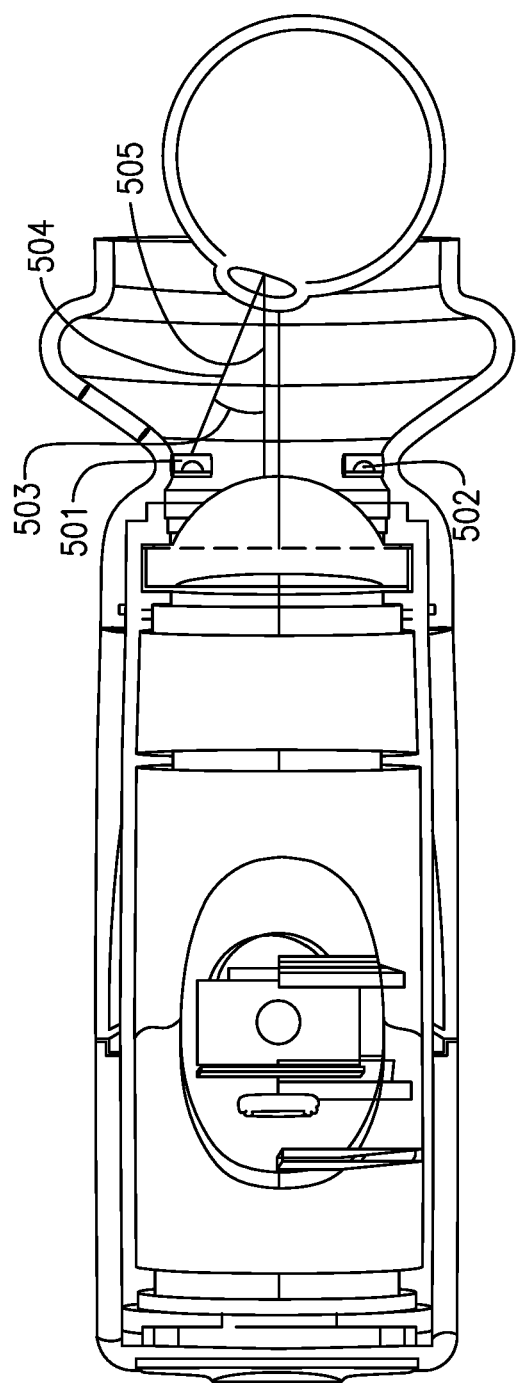
FIG. 5A is a top view, taken in section, of a medical device including an aiming/fixation light.

During examination of a patient's eye, it is often desired to have the patient's gaze directed at an angle so that portions of the patient's eye can be made visible to the caregiver for examination. Such a procedure can be made effective if the patient is provided a target upon which to fix his or her gaze. With reference to FIG. 5A, there is illustrated a top view cross-section of the medical diagnostic imaging device 10. In the present ophthalmic embodiment, the instrument 10 is provided with at least two LEDs 501, 502 that are selectively illuminated for providing a point upon which a patient undergoing an ophthalmic examination can fix their gaze. For example, if the user desires to obtain a view of the patient's optic disk, it is known that the optic disk is ideally visible through a pupil of the eye if the eye is fixed at a viewing angle 503 that is approximately 16 degrees inward 504, as measured from a line of sight 505 fixed directly forward. Thus, the LED 501 is illuminated for the patient to fixate his or her gaze while the optic disk in the patient's left eye is being examined, and the LED 502 is illuminated for the patient to fixate his or her gaze while the optic disk in the patient's right eye is being examined (illustrated in FIG. 4A). The LEDs 501, 502 can be electrically connected to the power supply and each can be manually switched on by the user using external controls provided on the ophthalmoscope 10.

In another embodiment, a plurality of LEDs can be positioned forward of the objective lens 14, as illustrated in FIGS. 5B-5C, in order to provide a range of fixation angles for the patient. As shown and using a plurality of individually illuminable LEDs e.g., 506, 507 that are arranged along a circular die 508, a series of digital images can be captured of portions of the eye, e.g., through the undilated pupil, having different regions exposed for viewing with each fixation point. In one embodiment, the multiple LEDs can be replaced with multiple optical fibers, or multiple bundles of optical fibers, illuminated by LEDs or other light sources in a handle or other portion of the ophthalmoscope.

In one embodiment, a series of digital images of the retina can be captured each at a different viewing angle through an undilated pupil while the patient fixates on a different one of the illuminated LEDs positioned in the circular arrangement. The series of retinal digital images can then be stitched together as a single continuous digital image of the patient's retina. Using conventional digital image stitching algorithms, a larger field of view of the patient's retina can be generated for optimal examination using this technique.

With reference to FIGS. 6A-6B, there is illustrated an arrangement of optical components that allows examination of a larger region of a patient's retina 38. Two adjustments of optical components can be made to enable an illuminated field of view 603 of the patient's retina covering approximately 20 degrees that can be increased to a field of view 604 of approximately 35 degrees. First, the objective lens 14 is positioned closer to the patient's eye, from a first distance 601 of about 35 mm to a second distance 602 of about 20-21 mm. This positioning allows light rays converging at an apex 39 to enter the interior of a patient's eye 36 at a wider angle, and thereby allowing a greater region 604 of the retina 38 to be illuminated. Together with this adjustment, the aperture 21 and/or 25 of the light source 30 and/or 31, respectively, is increased by approximately 30-35%, such as by rotating aperture wheel 21, 25 (FIG. 1C) to position a larger aperture forward of the light source, or by adjusting a variable iris to increase its aperture, to allow a wider beam of light to pass through the aperture 21 and/or 25, through condensing lens 32 eventually passing through the objective lens 14 that is converged at the apex 39. The wider field of view of retina 38 improves a diagnostician's ability to perceive characteristics of the retina, which may indicate types of retinopathy associated with, for example, diabetes or detection of glaucoma. Similarly, a wider dispersal of light rays reflected by the patient's retina allows an image of the wider field of view to be captured for later examination or for archival purposes.

Figure 7:
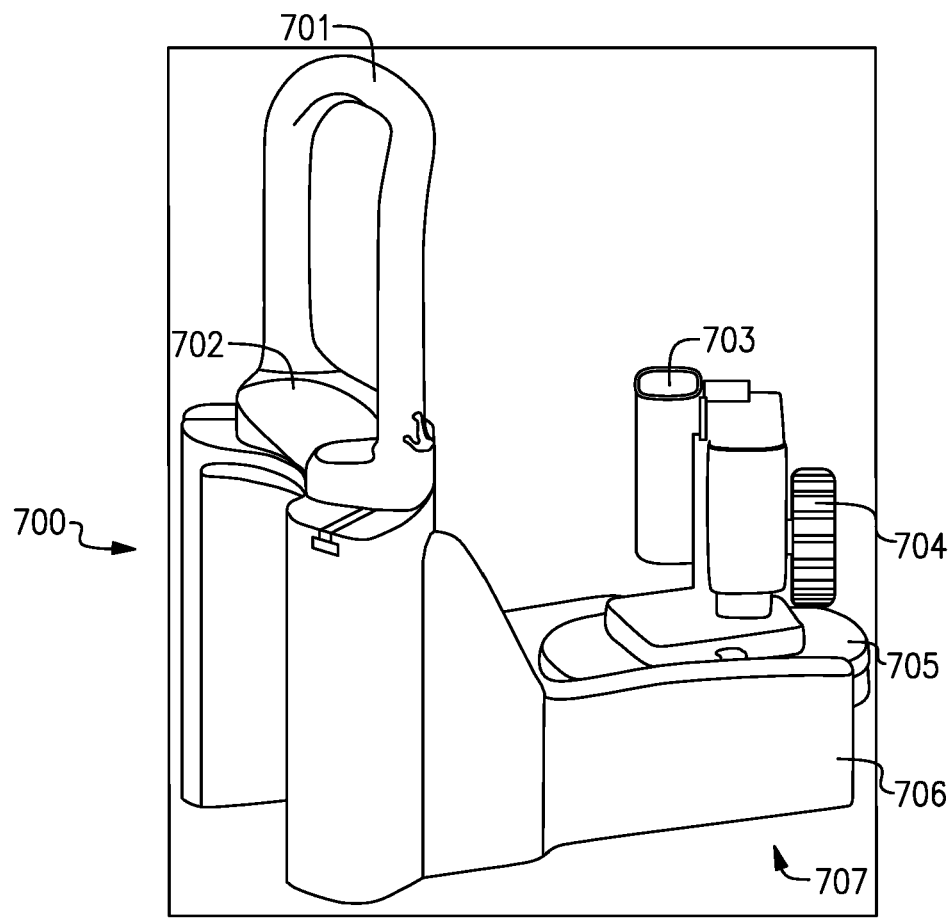
FIG. 7 is an front perspective view of a chin rest assembly made in accordance with an exemplary embodiment for use with the medical device of FIG. 1A.

In order to capture clear images during a medical examinations using a hand held medical diagnostic imaging instrument as described herein, it is typically preferred to utilize means for avoiding instrument or patient movement during a digital image capture step or during a digital image capture sequence. Any such movement can cause obvious blurring of digital images and less obvious decreased sharpness of captured digital images. One means for avoiding unnecessary movement of the instrument and/or the patient is by the use of a chin rest that can receive the instrument and enable proper placement and fixation of the patient. One embodiment of a chin rest is illustrated in FIG. 7, wherein chin rest portion is formed for receiving a patient's chin in resting contact with a portion 702. A separate spaced portion 701 is formed for simultaneously receiving a patient's forehead in contact therewith. Having the patient rest his or her head in this manner in the chin rest 700 allows the patient's head to be secured without movement. Simultaneously, the handle portion of the diagnostic imaging instrument 10 is inserted into portion 703 of the chin rest 700, which securely fixes the diagnostic instrument in place without movement or shaking. The instrument can then be rotated along a horizontal plane controlled by rotation of a base portion 705, and can also be vertically raised or lowered using handle 704. A bottom portion of chin rest 700 can be fitted with a surface for providing friction, such as rubber contacts or the like or alternatively, the assembly may be fitted with means for immovably attaching the chin rest 700 to a table top or other surface. The bottom portion 706 of the chin rest 700 may be made of a dense material for increasing an overall weight of the chin rest, thereby adding inertia that helps to prevent movement of the chin rest during use.

A second feature that is helpful to avoid unnecessary movement of the diagnostic imaging instrument is use of voice commands to trigger a single image capture or an image capture sequence. A microphone 15 (FIG. 1A) built into the instrument housing 29 detects the voice of the operator of the instrument. A voice recognition program stored in the processor 24 can therefore control certain features of operation, and avoiding the overuse of user actuated controls. According to one embodiment, the use of voice commands can control the exposure step for imager 20. Advantageously, the voice command image capture step avoids the requirement that an operator press a button or otherwise make physical contact with the medical diagnostic imaging instrument 10, thereby avoiding unnecessary movement of the instrument during digital image capture.

Referring to FIG. 8, there is illustrated a charging and data communication station 801 comprising a receptacle 803 for receiving and supporting a handle 44 of the hand held instrument 10. Charging and data communication station 801 includes a power cable 807 for connecting the station 801 to an electrical power source, and a communication cable 805 for connecting the station 801 to a processing system (not shown), such as a PC, laptop, server, or a hand held processing system device. As illustrated herein, communication cable 805 comprises a USB communication cable, but may comprise any of several communication cables, such as a PCI cable, an Ethernet cable, or an ePCI cable, for connecting the station 801 to processing system such as a PC, laptop, server, or other hand held processing system device such as a smart phone or tablet computer. Contained within housing 804 of the station 801 are charging and data control electronics 806 for selectively controlling a charging function and a data transfer function of charging and data communication station 801. A bottom of the handle 44 of the instrument 10 may comprise a mating connector for completing a mating connection with the station 801 terminal 802 whereby two way data transfers between the medical diagnostic imaging instrument 10 and a processing system connected via communication cable 805 can take place. Such data transfers can include digital images captured and stored in the instrument 10 being transferred to the connected processing system, and software upgrades for use by the processor 42 of the hand held medical diagnostic imaging instrument 10 transferred from the connected processing system. Such data transfers can take place with or without power cable 807 being connected to a power source such as provided, for example, in a USB compliant communication cable. If the power cable 807 is connected to a power source a charging current controlled by electronics 806 will supply voltage at a stepped down voltage as necessary to fully charge the imaging instrument 10. Alternatively, if the hand held medical diagnostic instrument 10 comprises a wireless data communication capability, the data transfers described above can take place without use of terminal 802 of data communication station 801.

Figure 10:
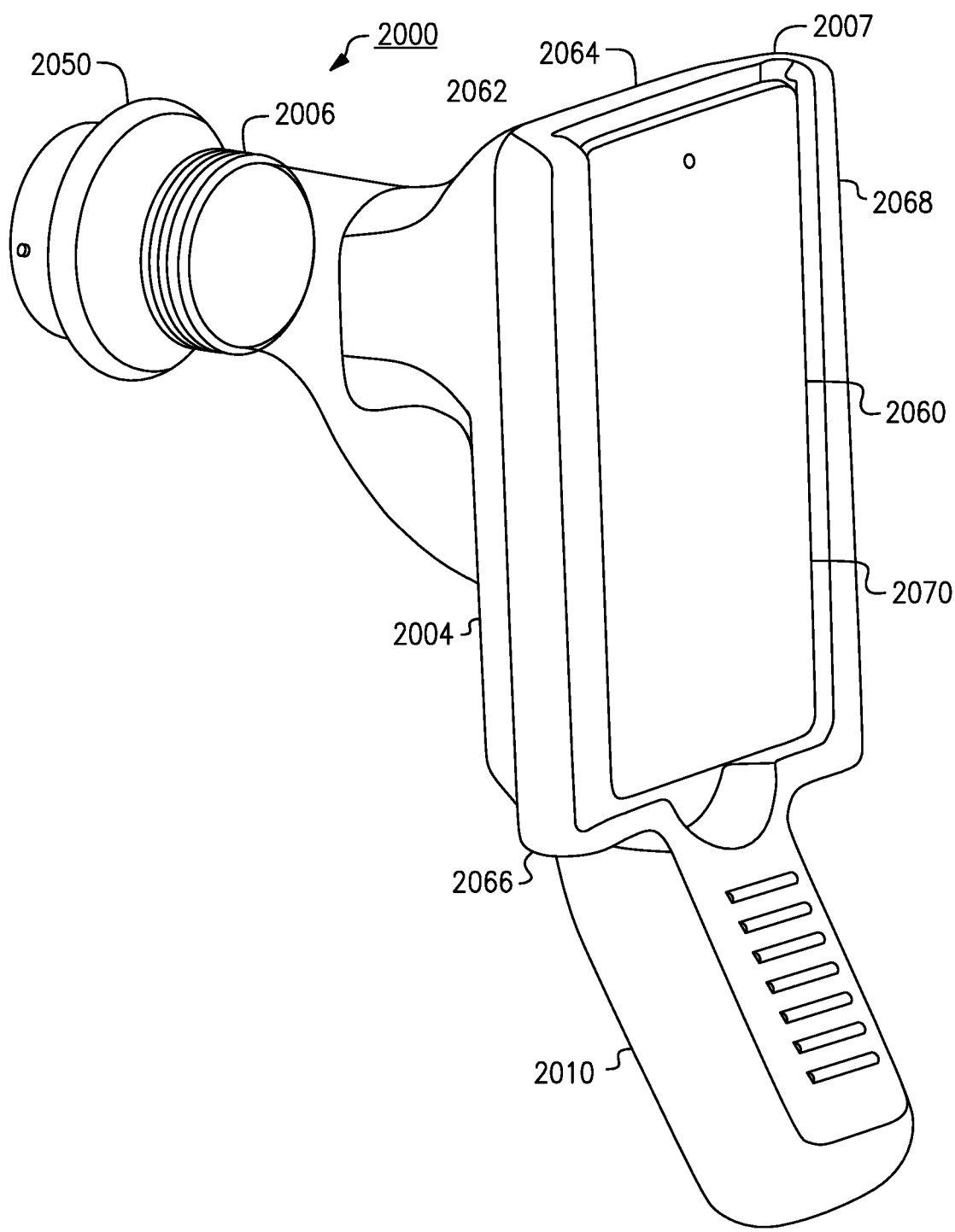
FIG. 10 is a rear perspective view of another medical device having a peripheral device releasably incorporated therewith.
Figure 11:
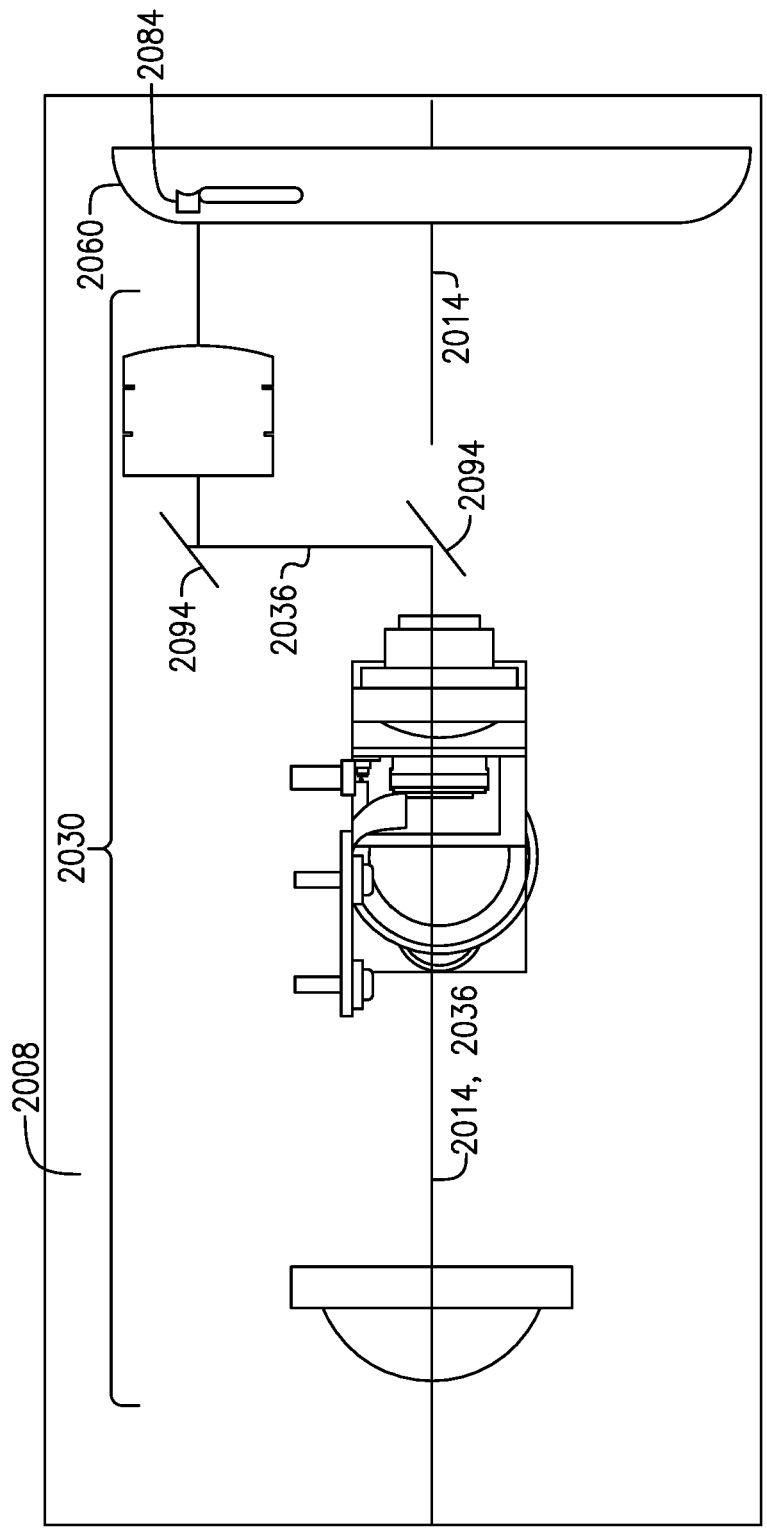
FIG. 11 is a schematic view of a configuration of the optical system within the medical device of FIG. 10, relative to an electronic imager of an attached peripheral device.
Figure 12:
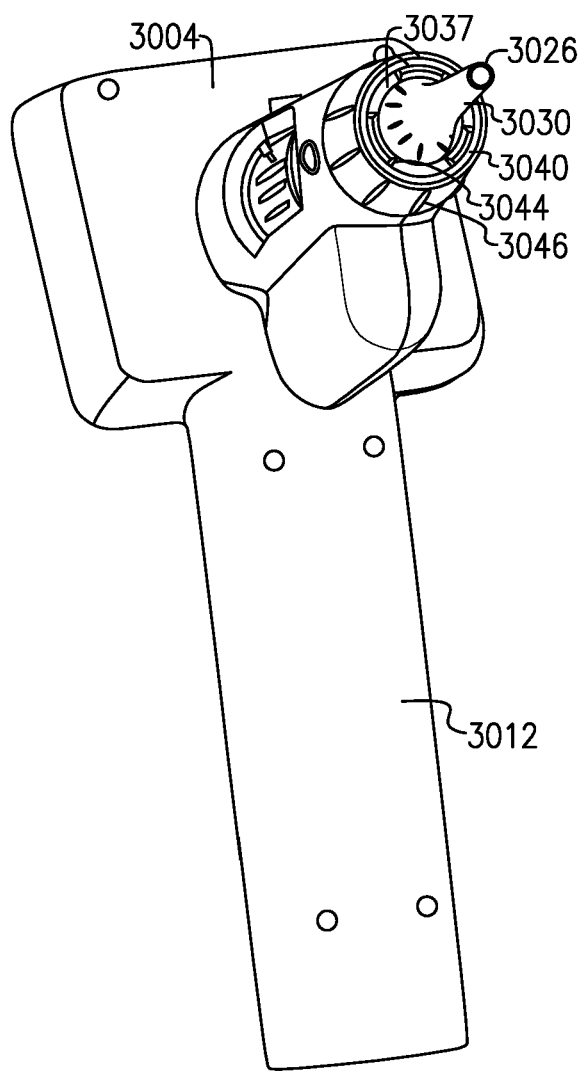
FIG. 12 is a front perspective view of a medical device in accordance with another exemplary embodiment.
Figure 13:
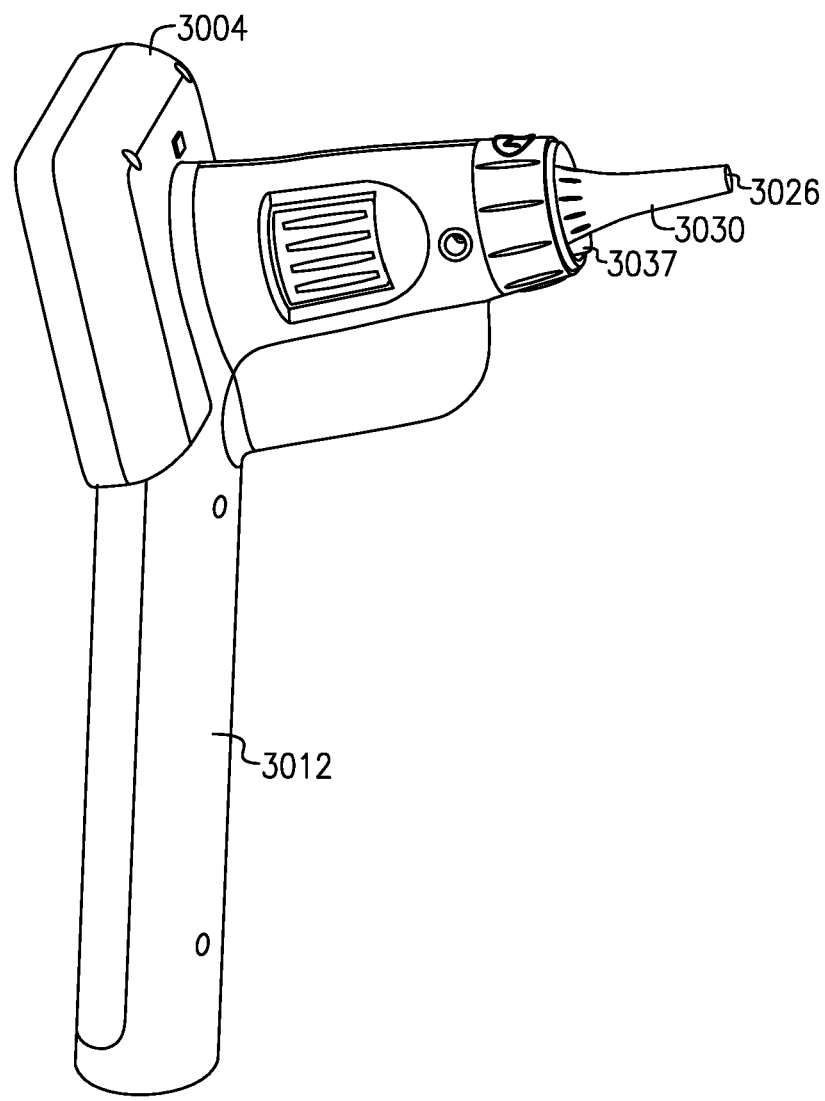
FIG. 13 is a side perspective view of the medical device of FIG. 12.

Referring to FIGS. 10 and 11, another exemplary embodiment of a medical device 2000 is herein described. The medical device 2000 depicted according to this exemplary embodiment is an ophthalmoscope, although the specific type of instrument can be varied as discussed herein. More specifically, the medical examination instrument 2000 is defined by a housing 2004 having a distal end 2006, a proximal end 2007, a handle 2010 and an interior 2008 (partially shown in FIG. 11) that is appropriately sized to retain, among other features, an optical system 2030 and an illumination system (not shown), each similar to those shown in FIGS. 1A and 1B. A patient interface 2050 in the form of an eye cup is releasably attached to the distal end 2006 of the housing 2004. According to this version and rather than integrating certain components within the instrument housing 2004, each of the electronic imager, processor and display are commonly provided within a peripheral device 2060 that is releasably attached to the proximal end 2007 of the housing 2004 and more specifically within a defined receptacle 2062. According to this specific embodiment, the peripheral device 2060 that is attached to the instrument housing 2004 is a smart phone. Alternatively, however, other devices could also be utilized, such as a tablet computer and/or an iPad or other device that includes an embedded portable camera. Referring to FIG. 11, the receptacle 2062 according to this embodiment is defined by an open ended cavity 2064 having an outer wall 2066 that is open with the exception of a lateral retaining edge 2068 enabling the display 2070 of the peripheral device 2060 to be visible therethrough as well as permitting access to various control features of the peripheral device 2060.

In addition and as depicted in FIG. 11, the contained electronic imager 2084 of the peripheral device 2060 may not be centrally located. In this instance and in order to provide an efficient and compact overall assemblage, the optical system 2030 of the instrument 2000 can be offset from the primary or center axis 2014 of the device 2000 using at least one mirror or lens 2094 so as to fold the imaging axis 2036 away from the primary axis 2014 of the housing 2004 so as to provide optical alignment with the electronic imager 2084 of a retained peripheral device 2060.

In use, the additional processing power of the attached peripheral device 2060 provides synergies in regard to the herein described device 2000. The receptacle 2062 provides an effective mechanical and optical interface and in which images are transmitted wirelessly to the "cloud" or a dedicated IT infrastructure. Application software in the peripheral device 2060 enables the medical device 2000 to be operated using the user interface of the device or using the touch screen and controls of the peripheral device 2060.

Referring to FIGS. 12-16, another exemplary medical device is described. According to this version, the medical device is a digital otoscopic instrument. As in the preceding generic and ophthalmic versions previously discussed, the otoscopic instrument 3000 is defined by an instrument housing 3004 that includes an interior 3008 sized for retaining a plurality of components, as well as a handle 3012 that preferably enables a user to operate the instrument 3000 using a single hand.

The otoscope housing 3004 is further defined by a distal end 3016 and an opposing proximal end 3020, the former including a substantially frusto-conical distal insertion portion 3024 that is configured to enable the releasable attachment of a speculum tip element 3030, which is used as the patient interface for the foregoing instrument 3000. The speculum tip element 3030 is preferably a disposable molded plastic component that is defined by a frusto-conical configuration and which includes a hollow interior having open distal and proximal ends 3034, 3038. In use, the tip element 3030 is shaped to be releasably placed in overlaying relation onto the exterior of the distal insertion portion 3024. The tip element 3030 can be made from plastic materials that are recyclable. According to at least one version, the tip element 3030 can be made from a material that is biodegradable or treatable, as previously discussed, such that degradation occurs within a prescribed time period.

The speculum tip element 3030 further includes engagement features that permit releasable attachment including a set of circumferentially disposed ribs 3037 that are formed at the proximal end 3038 of the speculum tip element 3030 for engagement into a set of receiving slots 3044 that are provided on a retainer member 3040 of the instrument 3000 adjacent the distal insertion portion 3024. The retainer member 3040 includes a rotatable actuating knob 3046 disposed over the exterior of the retainer member 3040 wherein the speculum tip element 3030 is placed into engagement by aligning the proximal end 3038 of the tip element 3030 with the retaining member 3040 and twisting the tip element 3030 such that the ribs 3037 are moved into the slots 3044. Rotation of the actuating knob 3046 against a spring bias (not shown) causes an interior feature (not shown) of the knob 3046 to push the ribs 3044 from the receiving slots 3044 of the retainer member 3040 and the speculum tip element 3030 from the housing 3004. Further details relating to the attachment mechanism and the engagement features of the speculum tip element are provided in commonly owned U.S. Pat. Nos. 7,399,275 and 8,066,634, the entire contents of each herein being incorporated by reference.

The distal insertion portion 3024 of the herein described medical examination instrument 3000 includes a distal tip opening 3026 such that when attached to the insertion portion 3024, the open distal ends 3026, 3034 of the distal insertion portion 3024 and the speculum tip element 3030 are respectively aligned with one another along an imaging axis 3045 of the instrument 3000.

An imaging system 3050 disposed within the housing 3004 comprises a plurality of optical components that are linearly disposed along the imaging axis 3045, which according to this version is also coincident with the primary or center axis of the instrument 3000. These optical components include an objective lens doublet 3054 that is disposed at the distal end 3026 of the distal insertion portion 3024, as well as a set of intermediate relay lenses 3056 and an aperture stop, each fixedly disposed within a series of lens tubes that are axially interconnected with one another within the housing 3004. An additional relay lens 3058 is disposed adjacent the electronic imager 3087 as well as an objective doublet 3060 maintained by an air gap therebetween, the latter elements being separately retained within a separate enclosure. As discussed according to FIGS. 2A-2D and 9, a variable lens focus assembly such as a liquid lens, can be disposed in the optical train.

According to one version, the initial focal point can be set manually, or automatically, to focus on the tympanic membrane of the middle ear to capture an image of the membrane. Thereafter, in quick succession and under processor control, the focal point can be incrementally adjusted by shifting one or more diopters to a focal plane above or beyond the tympanic membrane and an image captured thereof using a preselected illuminating light, f-stop, etc., as explained above, that optimally illuminates portions of the ear canal beyond the tympanic membrane, such as near infrared light.

An illumination system 3070 includes at least one light source 3074, which according to this embodiment is an incandescent bulb that is disposed adjacent the exterior of the housing 3004 in relation to the polished proximal end of a plurality of optical fibers (not shown) that further extend into the housing 3004 including distal ends (not shown) that are configured circumferentially about the interior of the distal opening 3026 of the distal insertion portion 3024 so as to project light to be directed through the speculum tip element 3030 and toward the target of interest.

Other alternative configurations regarding the type and placement of light sources are intended herein. For example and in lieu of an incandescent bulb, a ring-like configuration of LEDs can be disposed at the distal end of the insertion portion 3024, the LEDs being maintained at the distal periphery of the insertion portion 3024 between the optics and the interior wall of the insertion portion. This particular configuration is advantageous in that the LEDs provide sufficient illumination and further act to prevent condensation/fogging of the optical system, particularly the distally placed objective lens 1054, at the time of examination. This arrangement further assists significantly with heat dissipation. By providing a plurality of LEDs, the amount of illumination of each LED can be controlled using a rheostat or similar function with the additional option of selecting specific LEDS at any one time. For example, in a ringlet of 8 LEDS, only 4 center disposed LEDS could be used in accordance with one embodiment depending on the application. In another version, the LEDs can emit light of different wavelengths relative to each other.

According to this latter embodiment, the speculum tip element 3030 is fabricated from an optically clear and biocompatible material, such as polyethylene or polypropylene, and in which the application of light from the LED ring causes conduction of light throughout the entire speculum tip element 3030 due to the optically clear nature thereof. According to one version, the tip element can be treated with an additive, such as Green Solutions PPI-BD-0301 or Oxo-Degrader, enabling biodegradability after a prescribed time period.

An electronic imager 3087 is aligned with the imaging axis 3045 at the proximal end 3020 of the housing 3004 according to this embodiment, the imager 3087 being configured to capture at least one digital image of a target of interest. According to this version, the electronic imager 3087 is a CCD or CMOS imaging element. The optical system directs the image of the target of interest to the imager 3087, which is arranged on a printed circuit board, and which according to this embodiment further supports a processor (not shown) connected therewith. The positioning of the objective lens 3054 and the aligned optical components further creates a distal entrance pupil that prevents vignetting while also permitting a field of view in which the entire tympanic membrane can be viewed all at once when the speculum tip element is placed within the ear of a patient (not shown). Additional details regarding the optical system, including the distal entrance pupil is provided in U.S. Pat. No. 7,399,275, the entire contents of which are herein incorporated by reference.

A display 3090 is electrically connected to the electronic imager 3087 according to this exemplary embodiment by means of a flexible circuit 3091 attached to the printed circuit board and in which according to this embodiment, the display 3090 is also aligned along the primary axis of the instrument 3000 and mechanically and electrically integrated into the proximal end 3020 of the housing 3004. Alternative positioning of this latter component, however, is possible as is shown according to FIGS. 17-19, which depict medical examination instruments 3000A, each having integrated displays 3090A that are disposed above the remainder of the housing 3004A. Other suitable configurations are possible.

Figure 14:
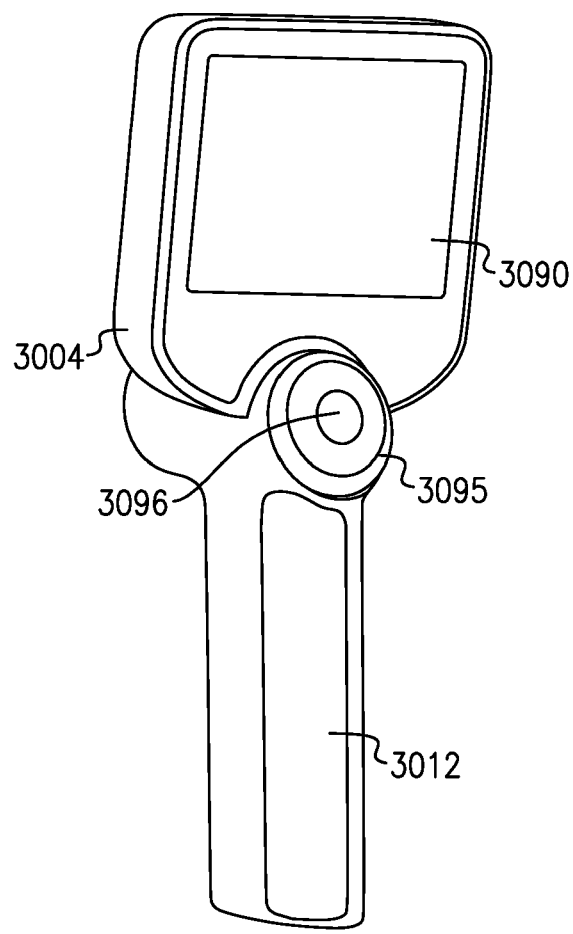
FIG. 14 is a rear perspective view of the medical device of FIGS. 12 and 13.
Figure 15:
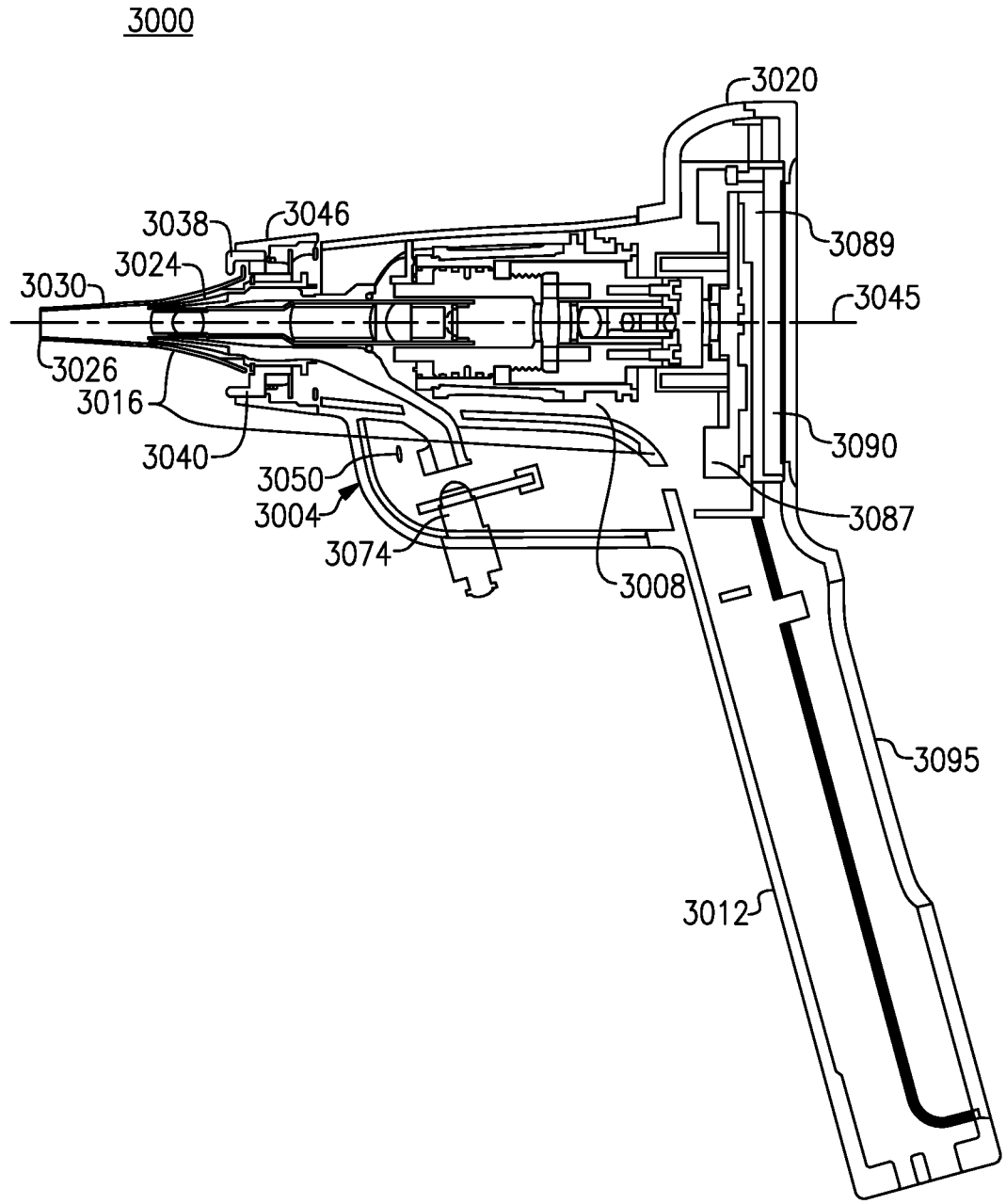
FIG. 15 is a side elevational view, taken in section of the medical device of FIGS. 11-14.
Figure 16:
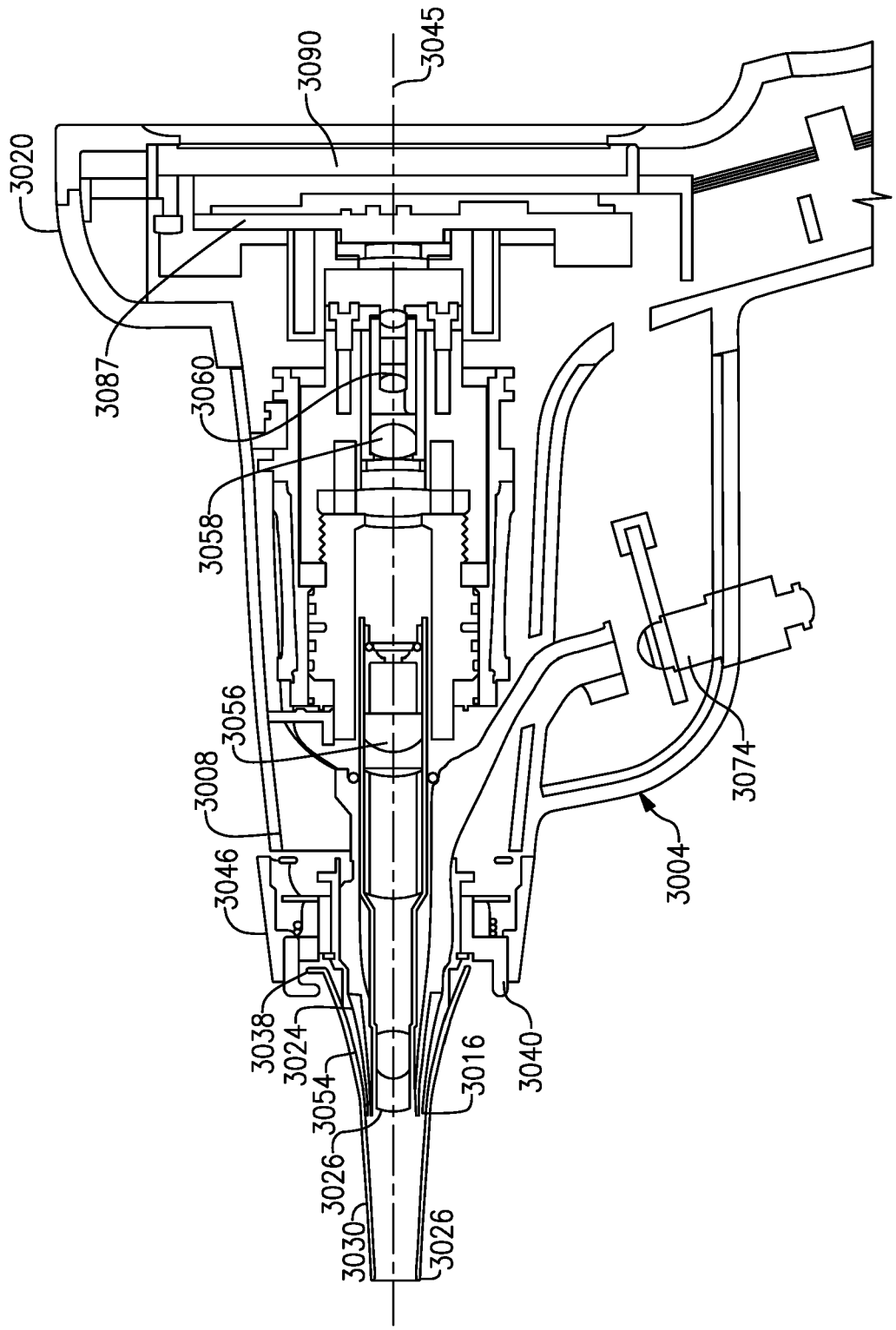
FIG. 16 is an enlarged sectioned view of a portion of the medical device of FIG. 15.
Figure 17:
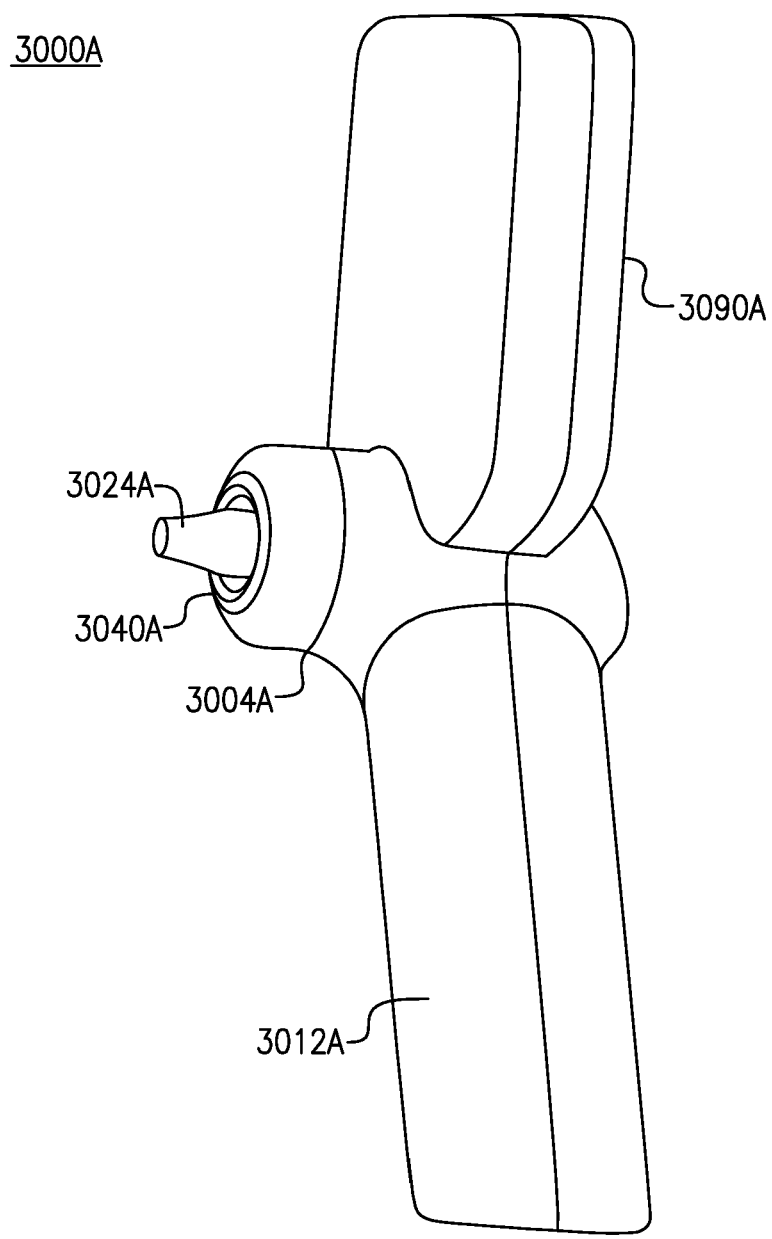
FIG. 17 is a front perspective view of a medical device in accordance with another exemplary embodiment.

The processor is electrically interconnected to each of the foregoing components in order to receive, store and transmit images captured by the electronic imager 3087, as well as operate the instrument 3000 using a user interface 3095 which is provided on the handle 3012 as shown in FIG. 15 or alternatively at the proximal end 3020 of the housing 3004 adjacent the display, as depicted in FIG. 14. The user interface 3095 includes at least one user actuable control member 3096. These members can permit capture, review of images captured, deletion of images, as well as those for powering the device. Relative axial movement between the electronic imager 3087 and at least one of the optical elements 3058, 3060 enables focusing of the herein described instrument 3000. Alternatively, a variable focus lens assembly, as discussed at FIGS. 2A and 2B, can be disposed within the defined optical train and enable dynamic on the fly focusing automatically. In addition and in connection with same, the focus position of the at least one liquid lens can be suitably adjusted by one or more diopters on either side of a nominal focus position such that the depth of focus can be selectively changed. The foregoing feature enables the target of interest to be adjusted, for example, to permit viewing the tympanic membrane and other areas within the ear for detection of infection (i.e., otitis media) when using different spectral light sources in which subsurface effects can readily detected. The use of spectral imaging for observing subsurfaces of a targeted body part is described in U.S. Pat. No. 9,001,326, entitled Method and Apparatus for Observing Subsurfaces of a Target Material, issued Apr. 7, 2015, which is hereby incorporated by reference in its entirety.

The herein described otoscope 3000 is powered directly through a contained portable power supply, such as at least one rechargeable battery or the inclusion of a super capacitor, such as previously described and preferably retained within a defined cavity in the handle 3012. Though the present embodiment relates to the inclusion of all related components on or within the housing 3004, it will be readily understood that the electronic imager, processor (or at least a portion of the functionality thereof) and display can alternatively be provided in a separate peripheral device such as a smart phone or a tablet computer that can be releasably attached to the housing 3004, and as previously described with reference to FIGS. 10 and 11.

Figure 9:
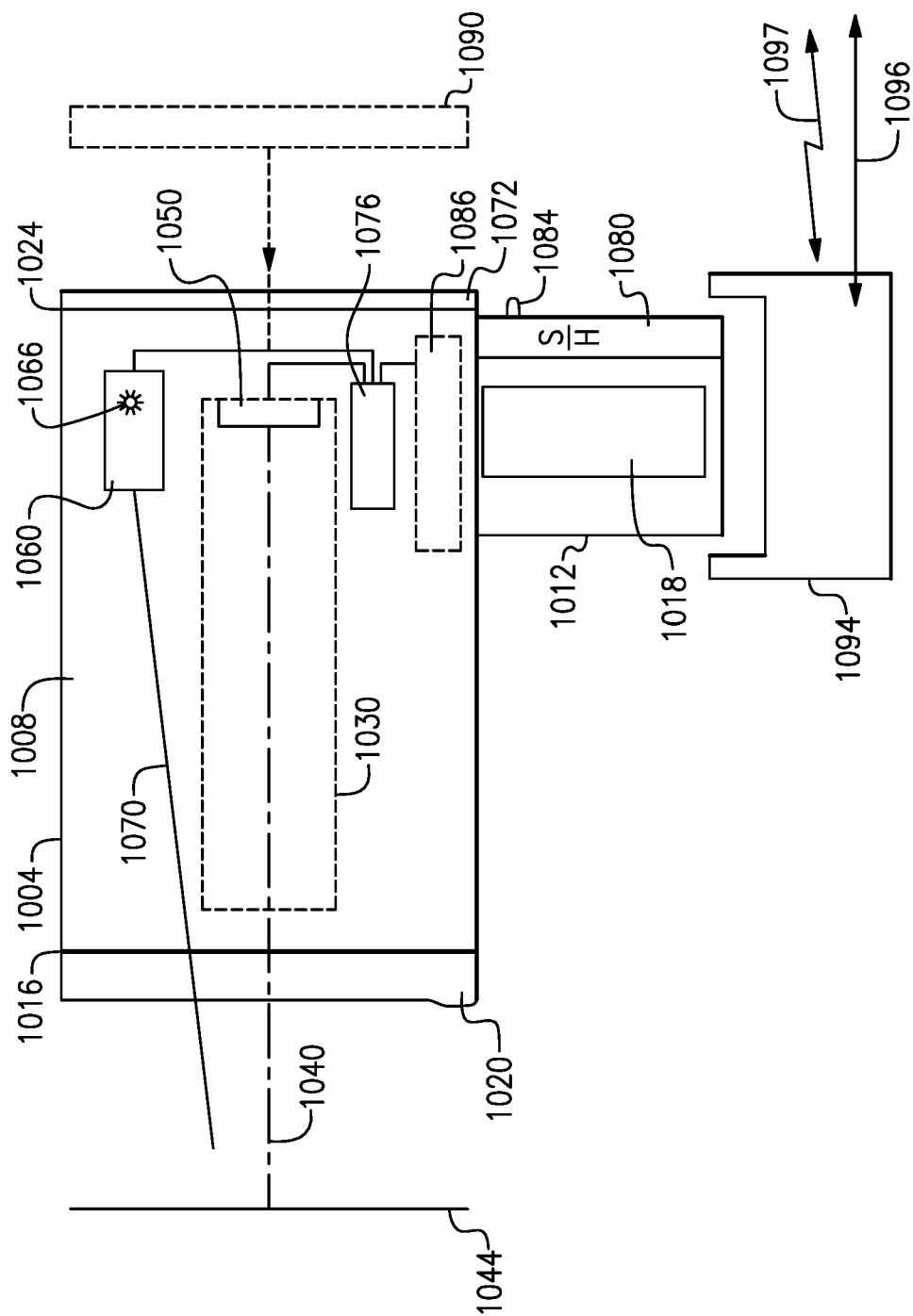
FIG. 9 depicts a generic schematic diagram of medical devices in accordance with the present invention.

The herein examination instrument 3000 can further be used, for example, with the docking stations such as those depicted in FIGS. 8 and 9 in order to enable charging of the contained portable power supply, as well as to facilitate data/image transfer to a remote device or station.

Referring to FIGS. 20-23, a skin measuring microscope device or instrument version is herein described in accordance with an exemplary embodiment. As in the preceding versions described herein, the skin measuring microscope 4000 of this embodiment comprises an instrument housing 4004, as well as a handle 4008 extending from a lower portion of the housing 4004 to preferably enable the instrument 4000 for single-handed operation. The handle 4008 further includes a defined interior that retains a compact power source 4012, which can include a set of rechargeable batteries or alternatively can include a super capacitor, as previously discussed. The remainder of the instrument housing 4004 also includes an interior 4014 that is configured and sized to retain a plurality of components, which according to this embodiment include an optical system 4020, an electronic imager 4050, a processor, an illumination system and a display 4080, each of the foregoing being integral to the housing 4004 or disposed in relation thereto.

The optical system 4020 comprises a plurality of optical components including a first lens 4024, a second lens 4027 and an aperture plate 4028 disposed between the first and second lenses that combine to form an air gap objective doublet and aligned optically with the electronic imager 4050 along an imaging axis 4026. The optical system according to this embodiment is configured to provide optimal focus based on an image plane formed at the distal end of a flexible patient interface and upon compression thereof onto the skin surface (not shown) of a patient. The electronic imager 4050, which is supported on a printed circuit board as well as the processor (not shown), is also aligned with the optical axis 4026 of the instrument 4000 and interconnected via the processor to the display 4080, which according to this specific embodiment is integrally mounted to an opposing proximal end 4007 of the housing 4004. Other arrangements such as those shown in FIGS. 17-19 can also be utilized.

The illumination system includes at least one light source which according to the present embodiment includes a plurality of LEDs 4044, such as white LEDs, that are arranged in a ring-like configuration at the distal end 4006 of the instrument housing 4004 and adjacent the patient interface 4060. At least one filter (not shown) can be included relative to the light source.

The flexible patient interface 4060 is configured to make contact with the skin of the patient (not shown) and according to a preferred version, is separably attached to the distal end 4006 of the instrument housing 4004. According to another version, the patient interface 4060 is made from a material, such as polyethylene or polypropylene or other suitable material or combination of suitable materials, that enable recyclability and reuse. The patient interface 4060 according to this embodiment is a cylindrical section that extends distally from the instrument housing 4004 when attached as shown herein and wherein the flexible nature of the interface 4060 permits limited compression of same when in engagement with a skin surface for examination.

A user interface 4090 is formed on the exterior of the handle 4008 of the instrument housing 4004, including at least one user-actuable element 4092, such as a button or switch that enables control of at least one operational feature of the herein described instrument 4000. Alternative arrangements to simplify the number of controls required by this interface, such as previously described, should be readily apparent including but not limited to voice control, use of positional sensors and the like. According to the herein described embodiment, each of the foregoing components (i.e., illumination system, electronic imager, display) are integrated within the housing 4004 and are electrically coupled to the processor. Alternatively, the electronic imager, display and processor (or at least certain functional aspects thereof) can be separately provided in a peripheral device (not shown) that can be attached and configured relative to the optical system and the processor, as previously described and shown in FIGS. 10 and 11.

In operation and according to this embodiment, the patient interface 4060 can be secured as a disposable component that is separate from the remainder of the assembly and which is placed in releasable fashion onto the distal end of the instrument housing 4004. Alternatively, the patient interface can already be provided on the housing either as a releasable or as an integral component. In terms of disposability, the interface can be made from a material that is biodegradable or can be treated with an additive that permits biodegradability after a predetermined time period. The handle 4012 of the instrument 4000 is gripped and the attached flexible patient interface 4060 is placed into intimate contact against the skin of the patient (not shown). Pressure is applied so as to compress the flexible patient interface to form a light seal and wherein the optics within the housing 4004 are preferably arranged to provide optimal focus based on axial compression of the patient interface 4060. The instrument 4000 is enabled using the user interface 4090, which activates the electronic imager 4050, the processor 4070, the LED array 4044 and the display 4080. The light that is emitted by the LED array 4044 is directed at the skin area of interest and images can be viewed on the display 4080 and subsequently captured and stored. According to at least one version, various characteristics of skin-related conditions can be measured in which the processor can include resident software that is configured to measure at least one characteristic of the skin-related condition (color, edge irregularity (shape), size, etc.) and compares at least one characteristic to stored thresholds. In addition, the processor can include memory that permits later images of the same area of skin to be re-measured and compared for changes to a condition of interest (e.g., scar, mole, wart, lesion, etc.) using the same measurement scales or fiducial marks or by comparing prior and current images.

Recharging of the contained portable power supply 4012 for the herein described medical examination instrument 4000 can be performed using a docking station, similar to that previously discussed herein and shown in FIGS. 8 and 9. The docking station may include at least one data port that permits image data transfer from the instrument when docked. An indicator (not shown) on the instrument housing 4004 is illuminated to indicate the state of data transfer. Alternatively, data can be directly transferred from the herein described instrument 4000 using wired and/or wireless transmission means. For example, the herein described instrument handle can include a USB or similar data port according to an alternative version or can include a wireless antenna to transfer data and to receive status changes to operating software and/or operating protocol, as needed.

According to another version and in lieu of a handle, the instrument housing can assume a tubular, substantially cylindrical or similar shape and in which the user can directly grip the exterior of the instrument. According to this design, the skin measuring microscope is similar in appearance to that of a loupe, but without an eyepiece; that is, an electronic imager and display are used in lieu of an eyepiece. The portable power supply according to this version is also disposed within the interior of the housing.

Figure 24:
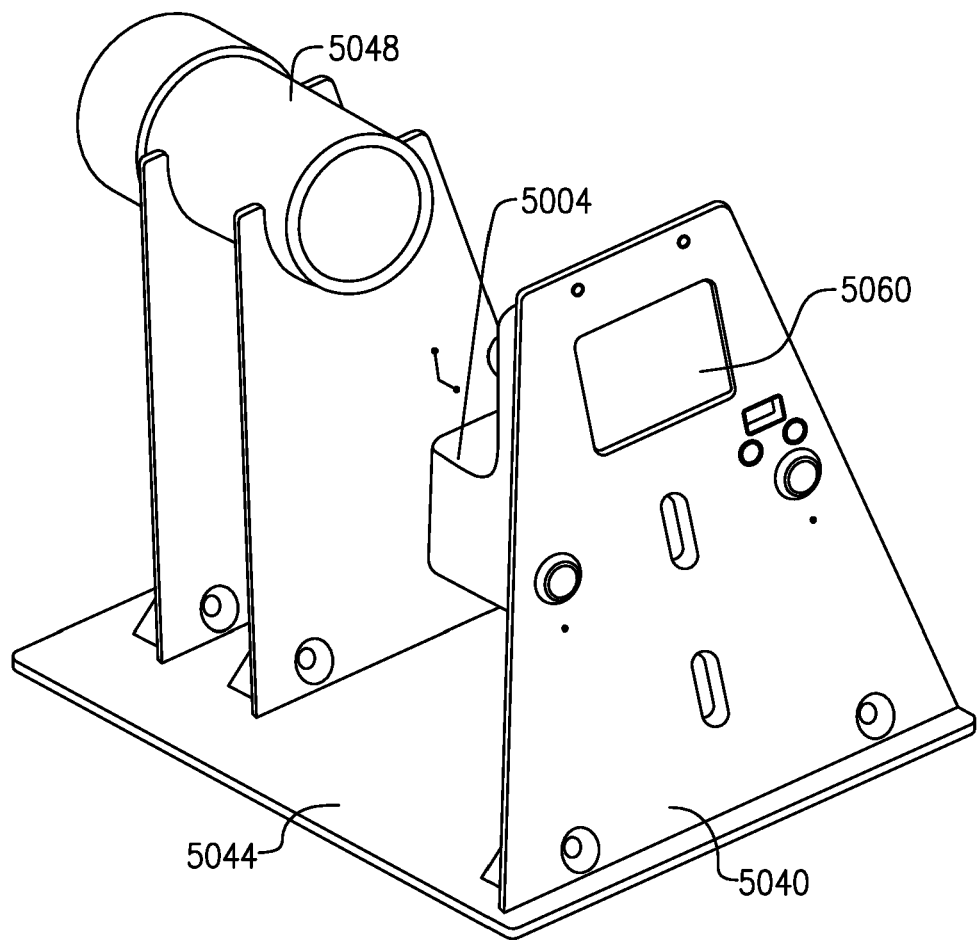
FIG. 24 is a rear perspective view of a medical device made in accordance with another exemplary embodiment and as mounted in a test fixture.
Figure 25:
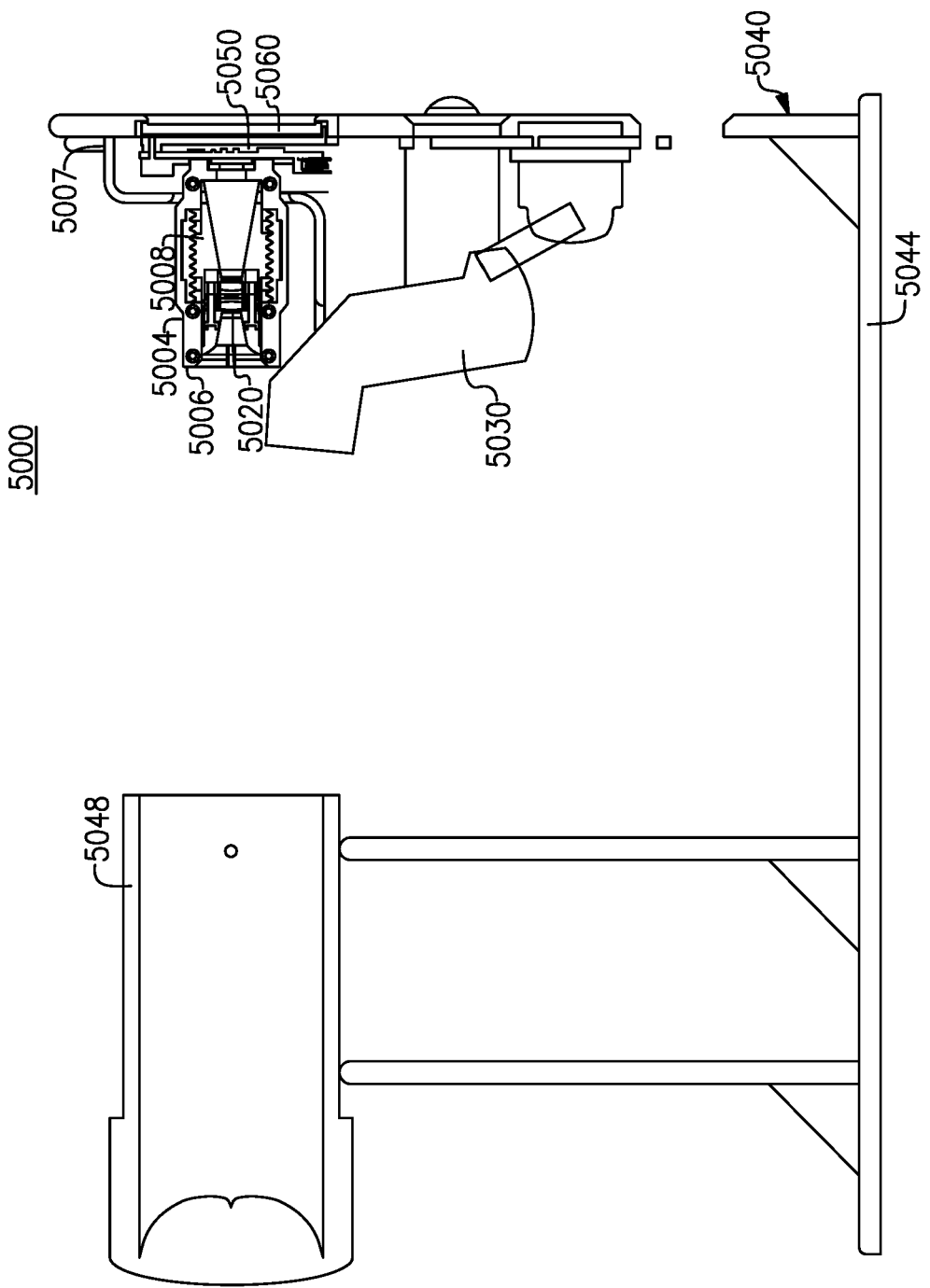
FIG. 25 is a side sectioned elevational view of the medical device of FIG. 24, as depicted within the test fixture.
Figure 26:
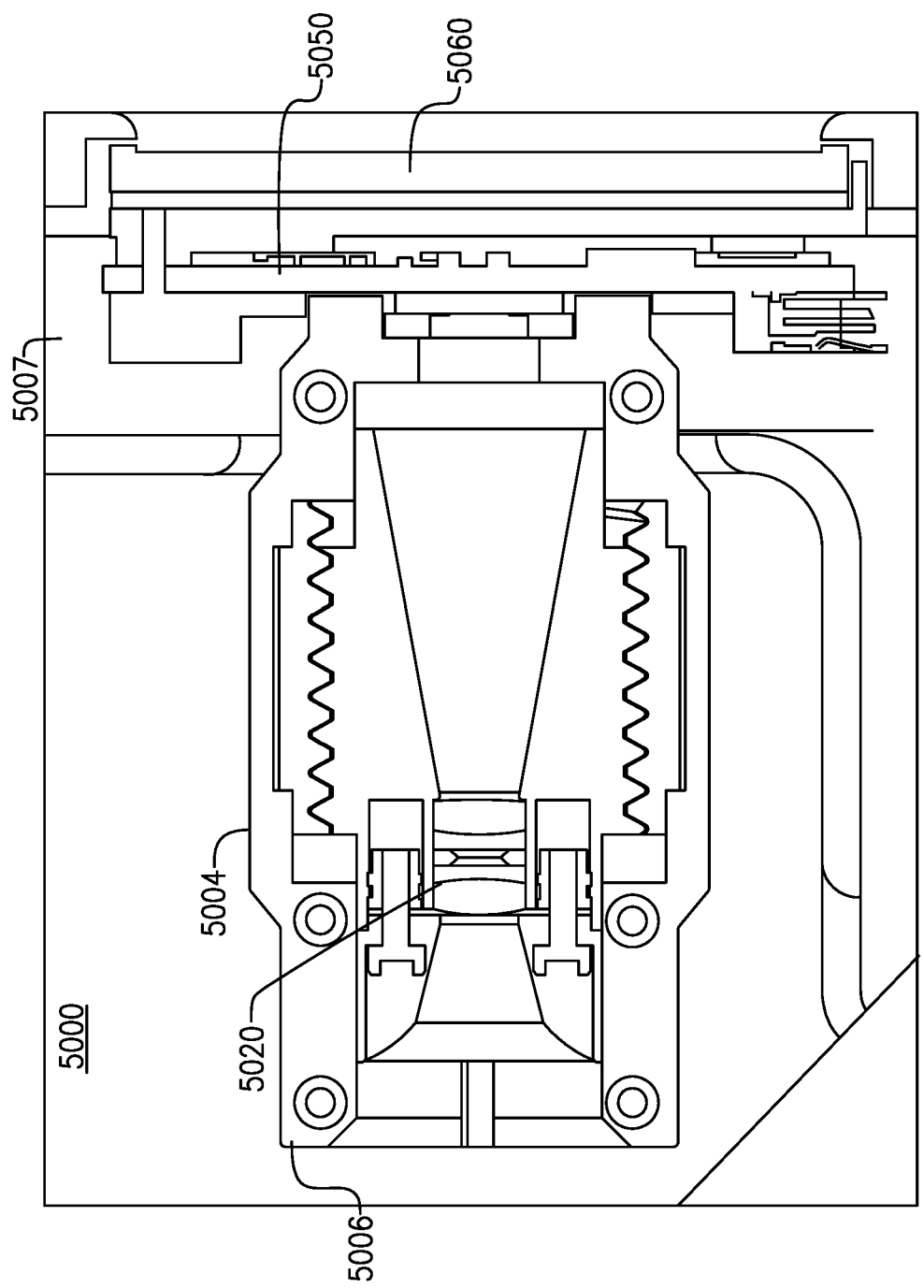
FIG. 26 is an enlarged portion of the sectioned view of the medical device of FIG. 25.

Referring to FIGS. 24-26, there is shown a colposcopic version of a medical examination instrument that is made in accordance with yet another exemplary embodiment. Reference is made herein to U.S. Pat. Nos. 6,359,677 and 6,147,705, incorporated by reference in their entirety that relate to the general aspects of an electronic colposcope. As in the preceding versions described herein, the colposcope 5000 is defined by a housing 5004 (partially shown in this embodiment) having an interior 5008 that is configured to retain a plurality of components, including an illumination system 5030, an optical system 5020, an electronic imager 5050, a processor (not shown), a portable power supply (not shown) and a display 5060, each of which are retained or are integral to the housing 5004 (only partially shown) according to this embodiment. Further details relating to the housing and support of exemplary colposcopic instruments are provided in the above cross referenced patents.

The colposcope housing 5004 further includes a distal end 5006, as well as an opposing proximal end 5007 in which the housing 5004 and illumination system 5030 are each supportably mounted within a fixture 5040 having a test frame 5044 and in which target (i.e., a female cervix) is simulated herein by a separately and adjacently supported member 5048 disposed a predetermined working distance from the instrument housing 5004 and illumination system 5030.

According to this embodiment, the interior 5008 of the colposcope housing 5004 retains the optical system 5020, which includes a plurality of optical elements linearly disposed along an optical axis 5044 and further aligned with the electronic imager 5050 which is disposed in the proximal end of the housing 5004, the latter being maintained on a printed circuit board along with the processor (not shown). The illumination system 5030 is provided adjacent the housing 5004 and includes at least one coupled light source such as an arc lamp or other convenient source capable of producing sufficient illumination.

In use, illumination is directed along a defined illumination axis at the target of interest and in which reflected light from the target is directed along the optical axis 5044 to the imager 5087 disposed within the housing 5004 for viewing at the display 5060 as well as for capture. Filtering can be provided either in hardware or software, such as a green filter, to aid in cervical examinations.

Alternatively, a peripheral device (not shown) having an integrated electronic imager, display and processor could be separately attached in releasable fashion to the housing 5004 and wherein the electronic imager is aligned with the optical axis of the instrument 5000. An exemplary version of this concept is previously discussed herein and shown at FIGS. 10 and 11.

PARTS LIST FOR FIGS. 1-26

- 10 instrument
- 11 illumination system
- 12 imaging system
- 13 power supply
- 14 objective lens
- 16 imaging lens
- 18 focusing lens assembly (variable focus liquid lens assembly)
- 20 imager
- 21 aperture wheel
- 22 imaging axis
- 23 pupil
- 24 variable voltage control (lens voltage control)
- 25 aperture wheel
- 26 light cone
- 27 light cone
- 28 apex
- 29 housing
- 30 light source
- 31 light source
- 32 condensing lens
- 33 filter
- 34 mirror
- 35 illumination axis
- 36 eye
- 38 retina
- 40 display (display screen)
- 41 beam splitter
- 42 processor
- 50 liquid lens
- 51 lens, variable focus liquid
- 52 lens, variable focus liquid
- 54 variable iris
- 61 housing
- 62 transparent window
- 63 transparent window
- 64 first electrode
- 65 frusto-conical opening
- 66 conical insulating layer
- 67 second electrode
- 68 insulator
- 69 insulating liquid (liquid drop)
- 70 insulating liquid
- 71 reference curve
- 72 axis
- 74 dashed line
- 301 LED
- 302 LED
- 401 eyecup portion
- 402 slot, eyecup
- 1000 medical device
- 1004 housing
- 1008 interior
- 1012 handle
- 1016 distal end
- 1018 power supply, portable
- 1020 proximal end
- 1030 optical system
- 1034 optical components
- 1040 imaging axis
- 1050 electronic imager
- 1060 illumination system
- 1066 light source
- 1070 illumination axis
- 1072 display
- 1076 processor
- 1080 user interface (UI)
- 1084 actuable element
- 1086 positional sensor
- 1090 peripheral device
- 1094 docking station
- 1096 arrow
- 1097 arrow
- 2000 medical device
- 2004 housing
- 2006 distal end
- 2007 proximal end
- 2008 interior
- 2010 handle
- 2014 primary or center axis
- 2030 optical system
- 2036 imaging axis
- 2050 patient interface
- 2060 peripheral device
- 2062 receptacle
- 2064 open ended cavity
- 2066 outer wall
- 2068 lateral retaining edge
- 2070 display
- 2084 electronic imager
- 2094 folding mirror or lens
- 3000 medical examination instrument
- 3004 housing
- 3008 interior
- 3012 handle
- 3016 distal end
- 3020 proximal end
- 3024 distal insertion portion
- 3026 distal opening, insertion portion
- 3030 speculum tip element
- 3034 distal tip opening
- 3037 ribs, tip element
- 3038 proximal tip opening
- 3040 retaining member
- 3044 receiving slots
- 3045 imaging axis
- 3046 actuating knob
- 3050 optical system
- 3054 objective doublet
- 3058 relay lens
- 3060 objective doublet
- 3070 illumination system
- 3074 light source
- 3087 electronic imager
- 3089 flexible circuit
- 3090 display
- 3095 user interface
- 3096 control member
- 4000 medical instrument
- 4004 housing
- 4006 distal end
- 4007 proximal end
- 4008 handle
- 4014 interior, housing 4020 optical system
4024 objective lens element
4026 optical axis
4050 electronic imager
4060 patient interface
4080 display
4090 user interface
4092 actuable control member
5000 medical instrument
5004 housing
5006 distal end
5007 proximal end
5008 interior
5012 portable power supply
5020 optical system
5030 illumination system
5040 test fixture
5044 frame
5048 simulated target
5050 electronic imager
5060 display
5070 processor

The invention claimed is:

1. A skin measuring microscope comprising:
   a housing;
   an optical system comprising a plurality of optical components aligned along an imaging axis, said plurality of optical components including a first lens, a second lens and an aperture plate disposed between the first and second lens;
   an illumination system comprising a plurality of LEDs formed in a ringlet at a distal end of the housing;
   an electronic imager aligned along the imaging axis;
   a display connected to the electronic imager, enabling viewing of a skin area of interest; and
   a patient interface disposed at the distal end of the housing configured for contacting the skin area of interest, the patient interface being configured for limited compression against the skin area of interest wherein an image plane of the optical system is formed relative to a distal end of the patient interface, such that the limited compression of the patient interface creates a light lock for the illumination system, as well as an optimal focus for the optical system for viewing the skin area of interest.

2. The skin measuring microscope as recited in claim 1, in which the compressible patient interface is releasably secured to the housing.

3. The skin measuring microscope as recited in claim 1, in which the compressible patient interface is at least one of disposable and recyclable.

4. The skin measuring microscope as recited in claim 1, in which the display is disposed at a proximal end of the housing and substantially aligned along the imaging axis.

5. The skin measuring microscope as recited in claim 4, in which the display is integral to the housing.

6. The skin measuring microscope as recited in claim 1, in which the display is integral to the housing and is not aligned with the imaging axis.

7. The skin measuring microscope as recited in claim 1, further comprising a processor connected to the electronic imager, the processor being configured to process and store images received from the electronic imager.

8. The skin measuring microscope as recited in claim 7, in which the microscope is configured to transfer at least one stored image on the processor to a remote site.

9. The skin measuring microscope as recited in claim 8, further comprising a docking station sized and configured to receive the microscope, wherein the docking station is adapted to receive image data from the microscope.

10. The skin measuring microscope as recited in claim 9, wherein the image data is transferred to the docking station automatically upon connection of the microscope to the docking station.

11. The skin measuring microscope as recited in claim 7, wherein the processor is programmed to measure and scale at least one aspect of a skin surface under examination.

12. The skin measuring microscope as recited in claim 7, further comprising at least one positional sensor disposed relative to the housing and coupled to the processor,
   wherein detection of signals from the at least one positional sensor are used by the processor for controlling at least one feature of the microscope.

13. The skin measuring microscope as recited in claim 12, in which the at least one feature includes powering of the skin measuring microscope.

14. The skin measuring microscope as recited in claim 1, further comprising at least one feature that dissipates heat generated by the ringlet of LEDs.

15. The skin measuring microscope as recited in claim 1, further comprising a user interface, including at least one user actuable element, for operating the microscope.

16. The skin measuring microscope as recited in claim 15, in which the user interface includes at least one feature to control the amount of light emitted by the ringlet of LEDs.

17. The skin measuring microscope as recited in claim 1, further comprising at least one filter movable into at least one of the imaging axis and an illumination axis of the illumination system.

* * * * *